US008088797B2

(12) United States Patent
Barth et al.

(10) Patent No.: US 8,088,797 B2
(45) Date of Patent: Jan. 3, 2012

(54) SUBSTITUTED N-(4-CYANO-1H-PYRAZOL-3-YL)METHYLAMINE DERIVATIVES, PREPARATION THEREOF AND THERAPEUTIC USE THEREOF

(75) Inventors: Francis Barth, Paris (FR); Christian Congy, Paris (FR); Serge Martinez, Paris (FR); Murielle Rinaldi-Carmona, Paris (FR); Martine Vernhet, Paris (FR)

(73) Assignee: Sanofi-Aventis, Paris (FR)

( * ) Notice: Subject to any disclaimer, the term of this patent is extended or adjusted under 35 U.S.C. 154(b) by 113 days.

(21) Appl. No.: 12/490,735

(22) Filed: Jun. 24, 2009

(65) Prior Publication Data
US 2010/0041709 A1 Feb. 18, 2010

Related U.S. Application Data

(63) Continuation of application No. PCT/FR2008/000005, filed on Jan. 2, 2008.

(30) Foreign Application Priority Data

Jan. 5, 2007 (FR) ..................................... 07 00095

(51) Int. Cl.
*A01N 43/40* (2006.01)
(52) U.S. Cl. .................... 514/326; 514/212; 514/236.5; 514/341; 548/374.1; 548/377.1
(58) Field of Classification Search .................. 514/326, 514/212, 236.5; 548/374.1, 377.1, 375.1
See application file for complete search history.

(56) References Cited

U.S. PATENT DOCUMENTS

| 5,624,941 | A | * | 4/1997 | Barth et al. ................... 514/326 |
| 7,282,516 | B2 | * | 10/2007 | Barth et al. ................... 514/406 |

FOREIGN PATENT DOCUMENTS

| EP | 0576357 | 12/1993 |
| EP | 0656354 | 6/1995 |
| EP | 1571147 | 9/2005 |
| WO | WO 95/15316 | 6/1995 |
| WO | WO 00/46209 | 8/2000 |
| WO | WO 2004/052864 | 6/2004 |
| WO | WO 2005/000820 | 1/2005 |
| WO | WO 2005/073197 | 8/2005 |

OTHER PUBLICATIONS

Bouaboula, M., et. al., A Selective Inverse Agonist for Central Cannabinoid Receptor Inhibits Mitogen-Activated Protein Kinase Activation Stimulated by Insulin or Insulin-Like Growth Factor 1, The Journal of Biological Chemistry, vol. 272, No. 35, (1997), pp. 22330-22339.
Bouaboula, et. al., Stimulation of Cannabinoid Receptor CB1 Induces Krox-24 Expression in Human Astrocytoma Cells, The Journal of Biological Chemistry, vol. 270, No. 23, (1995), pp. 13973-13980.
Ducry, L., et. al., Synthesis of 1,2,5-Thiadiazolidin-3-One 1,1-Dioxide Derivatives and Evaluation of Their Affinity for MHC Class-II Proteins, Helvetica Chimica Acta—vol. 82, (1999), pp. 2432-2447.
Matier, W. L., et al., Sulfomoyl Azides, Hydrolysis Rates and Hypotensive Activity, Journal of Medicinal Chemistiy, (1972), vol. 15, No. 5 pp. 538-541.
Olson, R. E., et. al., Orally Active Isoxazoline Glycoprotein IIb/IIIa Antagonists with Extended Duration of Action, J. Med. Chem., (1999), vol. 42. pp. 1178-1192.
Rinaldi-Carmona, M., et. al. et al., SR141716A, a potent and selective antagonist of the brain cannabinoid receptor, FEBS Letters, (1994), pp. 240-244, vol. 350.
Rinaldi-Carmona, M., et. al., Biochemical and Pharmacological Characterisation of SR141716A, The First Potent and Selective Brain Cannabinoid Receptor Antagonist, Life Sciences, vol. 56, No. 23/24, pp. 1941-1947, (1995).
Rinaldi-Carmona, M., et. al., Characterization of Two Cloned Human CB1 Cannabinoid Receptor Isoforms, The Journal of Pharmacology and Experimental Therapeutics, vol. 278, No. 2, pp. 871-878, (1996).
Rinaldi-Carmona, M., et. al., SR147778 5-(4-Bromophenyl)-1-(2,4-Dichlorophenyl)-4-ethyl-N-(1-Piperidinyl)-1H-Pyrazole-3-Carboxamide), A New Potent and Selective Antagonist of the CB1 Cannabinoid Receptor: Biochemical and Pharmacological Characterization, The Journal of Pharmacology and Experimental Therapeutics, vol. 310, No. 3, (2004), pp. 905-914.
Tait, A., et. al., Synthesis, Biological Evaluation and Molecular Modelling studies on Benzothiadiazine Derivatives as PDE4 Selective Inhibitors, Bioorganic & Medicinal Chemistry, vol. 13, (2005), pp. 1393-1402.

* cited by examiner

*Primary Examiner* — Andrew D Kosar
*Assistant Examiner* — Valerie Rodriguez-Garcia
(74) *Attorney, Agent, or Firm* — Scully, Scott, Murphy & Presser, P.C.

(57) ABSTRACT

The present invention relates to compounds corresponding to formula (I):

(I)

NC—[pyrazole ring]—CH$_2$—N(R$_2$)—X—R$_1$, with R$_3$ and R$_4$ substituents on the pyrazole Wherein X, R$_1$, R$_2$, R$_3$ and R$_4$ are as defined herein. The invention further relates to preparation and therapeutic use of these compounds.

16 Claims, No Drawings

SUBSTITUTED N-(4-CYANO-1H-PYRAZOL-3-YL)METHYLAMINE DERIVATIVES, PREPARATION THEREOF AND THERAPEUTIC USE THEREOF

CROSS REFERENCE TO RELATED APPLICATIONS

This application is a continuation of International application No. PCT/FR2008/000,005, filed Jan. 2, 2008, which is incorporated herein by reference in its entirety; which claims the benefit of priority of French Patent Application No. 07/00, 095, filed Jan. 5, 2007.

BACKGROUND OF THE INVENTION

1 Field of the Invention

The present invention relates to substituted N-(4-cyano-1H-pyrazol-3-yl)methylamine derivatives, their preparation, and their application in therapy.

2. Description of the Art

Diphenylpyrazole derivatives exhibiting an affinity for cannabinoid $CB_1$ receptors have been described in particular in patents U.S. Pat. No. 5,624,941, EP 0 576 357, EP 0 656 354, and EP 1 150 961 and in international patent application WO 2005/000 820.

There have now been new N-[(4-cyano-1H-pyrazol-3-yl)methyl]amine derivatives found which possess central and/or peripheral cannabinoid $CB_1$ receptor antagonist properties.

SUMMARY OF THE INVENTION

The present invention provides compounds conforming to the formula (I):

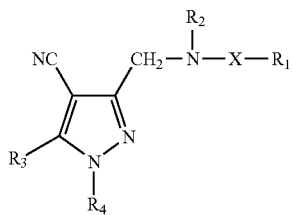

(I)

in which:
X represents a

, group, a

group, or a group $-SO_2N(R_5)-$;

$R_1$ represents:
an unsubstituted $(C_2-C_{12})$alkyl or a $(C_1-C_{12})$alkyl substituted one or more times by substituents selected independently from:
a) a fluorine atom;
b) a $(C_1-C_4)$alkoxY;
c) a $(C_3-C_7)$cycloalkyl;
d) a phenyl which is unsubstituted or substituted one or more times by substituents selected independently from a halogen atom, a group Alk, and a group OAlk;
e) a phenoxy, a phenylthio or a phenylsulfonyl in each of which the phenyl is unsubstituted or substituted one or more times by substituents selected independently from a halogen atom, a group Alk, and a group OAlk;
f) a pyridyloxy in which the pyridyl is unsubstituted or substituted one or more times by substituents selected independently from a halogen atom, a group Alk and a group OAlk;
g) a heterocyclic aromatic radical selected from a pyrrolyl, an imidazolyl, a pyrazolyl, a furyl, a thienyl, an oxazolyl, and a pyridyl, said radical being unsubstituted or substituted one or more times by substituents selected independently form a halogen atom, a group Alk, and a group OAlk;
$(C_3-C_{12})$ nonaromatic carbocyclic radical unsubstituted or substituted one or more times by substituents selected independently from a halogen atom, a group Alk, a group OAlk, a phenyl or a phenylsulfonyl, in both of which the phenyl is itself unsubstituted or substituted by a halogen atom;
a phenyl which is unsubstituted or substituted one or more times by substituents selected independently from a halogen atom, a group Alk, a group OAlk, a methylenedioxy, a group $-NHAlk$, a group $-N(Alk)_2$, a cyano, a nitro, a $(C_1-C_4)$alkylcarbonyl group, and a $(C_1-C_4)$alkoxy-carbonyl group; or from a phenyl, phenoxy, pyrrolyl, imidazolyl, pyrazolyl, oxazolyl, thiazolyl, triazolyl, thiadiazolyl or pyridyl radical, said radical being unsubstituted or substituted one or more times by a $(C_1-C_4)$alkyl;
a tetrahydronaphthyl which is unsubstituted or substituted by a $(C_1-C_4)$alkyl;
a 2,3-dihydrobenzofuranyl which is unsubstituted or substituted by a $(C_1-C_4)$alkyl;
a 3,4-dihydro-2H-pyranyl which is unsubstituted or substituted by a $(C_1-C_4)$alkyl;
a heterocyclic aromatic radical selected from a pyrrolyl, an imidazolyl, a pyrazolyl, a furyl, a thienyl, an oxazolyl, a pyridyl, an indolyl, and a 1,3-benzothiazolyl, said radical being unsubstituted or substituted one or more times by substituents selected independently from a halogen atom, a group Alk, and a group OAlk;
$R_2$ represents a hydrogen atom or a $(C_1-C_4)$alkyl;
$R_3$ represents a phenyl which is unsubstituted or substituted one or more times by substituents selected independently from a halogen atom, a group Alk and a group OAlk;
$R_4$ represents a phenyl which is unsubstituted or substituted one or more times by substituents selected independently from a halogen atom, a group Alk, and a group OAlk;
$R_5$ represents a hydrogen atom or a $(C_1-C_4)$alkyl; Alk represents a $(C_1-C_4)$alkyl which is unsubstituted or substituted one or more times by a fluorine atom.

The compounds of formula (I) may contain one or more asymmetric carbon atoms. They may therefore exist in the form of enantiomers or diastereoisomers. These enantiomers and diastereoisomers and also mixtures thereof, including the racemic mixtures, form part of the invention.

The compounds of formula (I) may exist in the form of bases or addition salts with acids. Such addition salts form part of the invention.

These salts are advantageously prepared with pharmaceutically acceptable acids, although the salts of other acids that are useful in the purification or isolation of compounds of formula (I) likewise form part of the invention.

The compounds of formula (I) may exist in the form of hydrates or solvates, i.e., in the form of associations or combinations with one or more molecules of water or with a solvent. Such hydrates and solvates likewise form part of the invention.

DETAILED DESCRIPTION OF THE INVENTION

A halogen atom means a bromine, chlorine, fluorine or iodine atom.

A $(C_1-C_4)$alkyl or $(C_1-C_{12})$alkyl, respectively, means a linear or branched alkyl radical of one to four carbon atoms or of one to twelve carbon atoms, respectively, such as the methyl, ethyl, propyl, isopropyl, butyl, isobutyl, sec-butyl, tert-butyl, pentyl, isopentyl, hexyl, isohexyl, heptyl, octyl, nonyl, decyl, undecyl or dodecyl radical.

A $(C_1-C_4)$alkoxy is a linear or branched alkoxy radical of one to four carbon atoms such as the methoxy, ethoxy, propoxy, isopropoxy, butoxy, sec-butoxy or tert-butoxy radical.

A $(C_3-C_7)$cycloalkyl is a cyclic alkyl group of 3 to 7 carbon atoms, such as the cyclopropyl, cyclobutyl, cyclopentyl, cyclohexyl or cycloheptyl group.

Nonaromatic $C_3-C_{12}$ carbocyclic radicals include mono- or polycyclic, fused, bridged or spiran radicals. Monocyclic radicals include $(C_3-C_7)$cycloalkyls. Fused, bridged or spiran di- or tricyclic radicals include, for example, norbornyl, bornyl, isobornyl, noradamantyl, adamantyl, spiro[5.5]undecyl, bicyclo-[2.2.1]heptyl, bicyclo[3.2.1]octyl, and bicyclo[3.1.1]-heptyl radicals.

Among the compounds of formula (I) that are subject matter of the invention, a distinction is made between:
  the compounds of formula (IA) in which —X— represents a —CO— group and the substituents $R_1$ to $R_4$ are as defined for the compounds of formula (I);
  the compounds of formula (IB) in which —X— represents a —CSNH— group and the substituents $R_1$ to $R_4$ are as defined for the compounds of formula (I);
  the compounds of formula (IC) in which —X— represents a group —SO$_2$N(R$_5$)— and the substituents $R_1$ to $R_5$ are as defined for the compounds of formula (I);
in the form of the base or of addition salts with acids, and also in the form of hydrates or solvates.

According to the present invention, preference is given to the compounds of formula (I) in which:
  X represents a

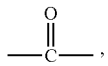

group or a

group
$R_1$ represents:
    an unsubstituted $(C_2-C_{12})$alkyl or a $(C_1-C_{12})$alkyl which is mono- or disubstituted by substituents selected independently from:
    b) a $(C_1-C_4)$alkoxy;
    c) a $(C_3-C_7)$cycloalkyl;
    d) a phenyl which is unsubstituted or mono- or disubstituted by substituents selected independently from a halogen atom, a group Alk, and a group OAlk;
    e) a phenoxy, a phenylthio or a phenylsulfonyl in each of which the phenyl is unsubstituted or mono- or disubstituted by substituents selected independently from a halogen atom, a group Alk, and a group OAlk;
    f) a pyridyloxy in which the pyridyl is substituted by a group Alk;
    g) a heterocyclic aromatic radical selected from a pyrrolyl;
  a $(C_3-C_7)$cycloalkyl which is unsubstituted or monosubstituted by a substituent selected from a group Alk, a group OAlk, and a phenyl or a phenylsulfonyl in both of which the phenyl is itself substituted by a halogen atom;
  a bicyclo[2.2.1]heptyl;
  a phenyl which is unsubstituted or is mono- or disubstituted by substituents selected independently from a halogen atom, a group Alk, a group OAlk, a methylenedioxy, a group —N(Alk)$_2$, a cyano, a $(C_1-C_4)$alkylcarbonyl, and a $(C_1-C_4)$alkoxycarbonyl; or from a phenyl or pyrrolyl radical;
  a 2,3-dihydrobenzofuranyl;
  a 3,4-dihydro-2H-pyranyl substituted by a $(C_1-C_4)$alkyl;
  a heterocyclic aromatic radical selected from a pyrazolyl, a furyl, a thienyl, an indolyl, and a 1,3-benzothiazolyl, said radical being unsubstituted or being monosubstituted or disubstituted with substituents selected independently from a halogen atom and a group Alk;
$R_2$ represents a hydrogen atom;
$R_3$ represents a phenyl which is monosubstituted by a halogen atom, or a group OAlk;
$R_4$ represents a phenyl which is mono- or disubstituted by a halogen atom;
$R_5$ represents a hydrogen atom or a $(C_1-C_4)$alkyl;
Alk represents a $(C_1-C_4)$alkyl which is unsubstituted or substituted one or more times by a fluorine atom;
in the form of the base or of addition salts with acids, and also in the form of hydrates or solvates.

In particular, preference is given to the compounds of formula (I) in which:
  X represents a

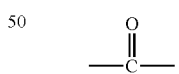

group or a

group,
$R_1$ represents:
    an n-butyl, a tert-butyl, a 1-ethylpropyl, a 1-propylbutyl, a methoxy(phenyl)methyl, a cyclopentylmethyl, a cyclohexylmethyl, a cyclohexyl(phenyl)methyl, a (3,4-dimethoxyphenyl)methyl, a 2-(4-methyl-phenyl)ethyl, a 2-[4-(trifluoromethyl)phenyl]ethyl, a 2,2- diphenylethyl, a 1-(2-chlorophenoxy)-1-methylethyl, a 1-(3-chlorophenoxy)-1-methylethyl, a 1-(4-chlorophenoxy)-1-methylethyl, a 1-(2-methylphenoxy)-1-methylethyl, a 1-(4-methylphenoxy)-1-methylethyl, a 1-methyl-1-[3-trifluoromethyl)phenoxy] ethyl, a 1-(2-methoxyphenoxy)-1-methylethyl, a 1-(3-methoxyphenoxy)-1-methylethyl, a 1-[(4-chlorophenyl)thio]-1-methylethyl, a 1-[(4-chloro-phenyl)sulfonyl]-1-methylethyl, a 1-methyl-1-[[5-(trifluoromethyl)pyridin-2-yl]oxy]ethyl, a 2,2-dimethyl-1-(1H-pyrrol-1-yl)propyl;

a 1-methylcyclopropyl, a cyclopentyl, a 1-(4-chlorophenyl)cyclopentyl, a 1-[(4-chlorophenyl)sulfonyl]cyclopentyl, a cyclohexyl, a 1-methyl-cyclohexyl, a 3-methoxycyclohexyl, a 4-methoxy-cyclohexyl, a cycloheptyl, a bicyclo[2.2.1]heptyl;

a phenyl, a 2-chlorophenyl, a 3-chlorophenyl, a 2,5-difluorophenyl, a 3,5-dimethylphenyl, a 4-tert-butylphenyl, a 4-(trifluoromethyl)phenyl, a 3-methoxyphenyl, a 4-methoxyphenyl, a 4-(trifluoromethoxy) phenyl, a 3-phenoxyphenyl, a 4-phenoxyphenyl, a 1,3-benzodioxol-5-yl, a 3-(dimethylamino)phenyl, a 4-cyanophenyl, a 3-acetylphenyl, a 4-acetylphenyl, a 4-(methoxy-carbonyl)phenyl, a 4-(1H-pyrrol-1-yl)phenyl;

a 2,3-dihydro-1-benzofuran-5-yl;

a 6-methyl-3,4-dihydro-2H-pyran-5-yl;

a 3-tert-butyl-1-ethyl-1H-pyrazol-5-yl, a 2-furyl, a 5-bromo-2-furyl, a 5-chloro-2-thienyl, a 5-methyl-2-thienyl, a 1H-indol-2-yl, a 1-methyl-1H-indol-2-yl, a 1,3-benzothiazol-6-yl;

$R_2$ represents a hydrogen atom;

$R_3$ represents a 4-chlorophenyl or a 4-methoxyphenyl;

$R_4$ represents a 2-bromophenyl, a 2-chlorophenyl, a 2,4-dichlorophenyl;

in the form of the base or of addition salts with acids, and also in the form of hydrates or solvates.

In particular, also, preference is given to the compounds of formula (IA) in which:

X represents a

group;

$R_1$ represents:

an n-butyl, a tert-butyl, a 1-ethylpropyl, a 1-propylbutyl, a methoxy(phenyl)methyl, a cyclopentylmethyl, a cyclohexylmethyl, a cyclohexyl(phenyl)methyl, a (3,4-dimethoxyphenyl)methyl, a 2-(4-methyl-phenyl)ethyl, a 2-[4-(trifluoromethyl)phenyl]ethyl, a 2,2-diphenylethyl, a 1-(2-chlorophenoxy)-1-methylethyl, a 1-(3-chlorophenoxy)-1-methylethyl, a 1-(4-chlorophenoxy)-1-methylethyl, a 1-(2-methylphenoxy)-1-methylethyl, a 1-(4-methylphenoxy)-1-methylethyl, a 1-methyl-1-[3-trifluoromethyl)phenoxy] ethyl, a 1-(2-methoxyphenoxy)-1-methylethyl, a 1-(3-methoxyphenoxy)-1-methylethyl, a 1-[(4-chloro-phenyl)thio]-1-methylethyl, a 1-[(4-chlorophenyl)sulfonyl]-1-methylethyl, a 1-methyl-1-[[5-(trifluoromethyl)pyridin-2-yl]oxy]ethyl, a 2,2-dimethyl-1-(1H-pyrrol-1-yl)propyl;

a 1-methylcyclopropyl, a cyclopentyl, a 1-(4-chlorophenyl)cyclopenyl, a 1-[(4-chlorophenyl)sulfonyl]cyclopentyl, a cyclohexyl, a 1-methyl-cyclohexyl, a 3-methoxycyclohexyl, a 4-methoxy-cyclohexyl, a cycloheptyl, a bicyclo[2.2.1]heptyl;

a phenyl, a 2-chlorophenyl, a 3-chlorophenyl, a 2,5-difluorophenyl, a 3,5-dimethylphenyl, a 4-tert-butylphenyl, a 3-methoxyphenyl, a 4-methoxyphenyl, a 4-(trifluoromethoxy)phenyl, a 3-phenoxyphenyl, a 4-phenoxyphenyl, a 1,3-benzodioxol-5-yl, a 3-(dimethylamino)phenyl, a 4-cyanophenyl, a 4-acetylphenyl, a 4-(methoxy-carbonyl)phenyl, a 4-(1H-pyrrol-1-yl)phenyl;

a 2,3-dihydro-1-benzofuran-5-yl;

a 6-methyl-3,4-dihydro-2H-pyran-5-yl;

a 3-tert-butyl-1-ethyl-1H-pyrazol-5-yl, a 2-furyl, a 5-bromo-2-furyl, a 5-chloro-2-thienyl, a 5-methyl-2-thienyl, a 1H-indol-2-yl, a 1-methyl-1H-indol-2-yl, a 1,3-benzothiazol-6-yl;

$R_2$ represents a hydrogen atom;

$R_3$ represents a 4-chlorophenyl or a 4-methoxyphenyl;

$R_4$ represents a 2-bromophenyl, a 2-chlorophenyl, a 2,4-dichlorophenyl;

in the form of the base or of addition salts with acids, and also in the form of hydrates or solvates.

In particular also, preference is given to the compounds of formula (IB) in which:

X represents a

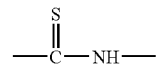

group;

$R_1$ represents:

a cyclohexyl;

a 4-(trifluoromethyl)phenyl, a 3-methoxyphenyl, a 4-cyanophenyl or a 3-acetylphenyl;

$R_2$ represents a hydrogen atom;

$R_3$ represents a 4-chlorophenyl;

$R_4$ represents a 2-chlorophenyl or a 2,4-dichlorophenyl;

in the form of the base or of addition salts with acids, and also in the form of hydrates or solvates.

Among the compounds of formula (I) that are subject matter of the invention, mention may be made in particular of the following compounds:

N-[[5-(4-chlorophenyl)-4-cyano-1-(2,4-dichlorophenyl)-1H-pyrazol-3-yl]methyl]-3,3-diphenylpropanamide;

N-[[5-(4-chlorophenyl)-4-cyano-1-(2,4-dichlorophenyl)-1H-pyrazol-3-yl]methyl]-4-(1H-pyrrol-1-yl)benzamide;

1-[[5-(4-chlorophenyl)-4-cyano-1-(2,4,dichlorophenyl)-1H-pyrazol-3-yl]methyl]-3-(3-methoxyphenyl)thiourea;

N-[[1-(2-chlorophenyl)-5-(4-chlorophenyl)-4-cyano-1H-pyrazol-3-yl]methyl]-3-[4-(trifluoromethyl)phenyl] propanamide;

N-[[1-(2-chlorophenyl)-5-(4-chlorophenyl)-4-cyano-1H-pyrazol-3-yl]methyl]-3,3-diphenylpropanamide;

2-(2-chlorophenoxy)-N-[[1-(2-chlorophenyl)-5-(4-chlorophenyl)-4-cyano-1H-pyrazol-3-yl]methyl]-2-methylpropanamide;

N-[[1-(2-chlorophenyl)-5-(4-chlorophenyl)-4-cyano-1H-pyrazol-3-yl]methyl]-2-methyl-2-(2-methylphenoxy) propanamide;

N-[[1-(2-chlorophenyl)-5-(4-chlorophenyl)-4-cyano-1H-pyrazol-3-yl]methyl]-1-[(4-chlorophenyl)sulfonyl]cyclopentanecarboxamide;

N-[[1-(2-chlorophenyl)-5-(4-chlorophenyl)-4-cyano-1H-pyrazol-3-yl]methyl]-4-(trifluoromethoxy)benzamide;

N-[[1-(2-chlorophenyl)-5-(4-chlorophenyl)-4-cyano-1H-pyrazol-3-yl]methyl]-4-cyanobenzamide;

2-(3-chlorophenoxy)-N-[[1-(2-chlorophenyl)-4-cyano-5-(4-methoxyphenyl)-1H-pyrazol-3-yl]methyl]-2-methylpropanamide;

in the form of the base or of addition salts with acids, and also in the form of hydrates or solvates.

In the text below, a leaving group is a group which can be easily cleaved from a molecule by the breaking of a heterolytic bond, with the departure of an electron pair. This group may thus be easily replaced by another group in the course of a substitution reaction, for example. Leaving groups of this kind are, for example, halogens or an activated hydroxyl group such as a methanesulfonate, benzenesulfonate, p-toluenesulfonate, triflate, acetate, etc. Examples of leaving groups and of references for their preparation are given in "Advances in Organic Chemistry", J. March, 3rd edition, Wiley Interscience, 1985, pp. 310-316.

In accordance with the invention, the compounds of the formula (I) can be prepared by a process which is characterized in that:

a compound of formula:

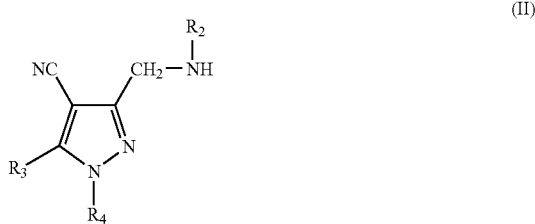

(II)

in which $R_2$, $R_3$, and $R_4$ are as defined for a compound of formula (I):

alternatively with an acid or a difunctional derivative of this acid of formula:

HOOC—$R_1$ (III)

in which $R_1$ is as defined for a compound of formula (I), when the aim 1s to prepare a compound of formula (I) in which —X— represents a —CO— group;

or with an isothiocyanate of formula:

S=C=N—$R_1$ (VII)

in which $R_1$ is as defined for a compound of formula (I), when the aim 1s to prepare a compound of formula (I) in which —X— represents a —CSNH— group;

or with a sulfamoyl chloride of formula:

ClSO$_2$N(R$_5$)R$_1$ (XVII)

in which $R_1$ and $R_5$ are as defined for a compound of formula (I), when the aim 1s to prepare a compound of formula (I) in which —X— represents a group —SO$_2$N(R$_5$)

When a compound of formula (II) is treated with the acid of formula (III) itself, this operation is carried out in the presence of a coupling agent which is used in peptide chemistry, such as 1,3-dicyclohexyl-carbodiimide or benzotriazol-1-yloxytris(dimethylamino)phosphonium hexafluorophosphate or benzotriazol-1-yloxytris(pyrrolidino)phosphonium hexafluorophosphate or 2-(1H-benzotriazol-1-yl)-1,1,3,3-tetramethyluronium tetrafluoroborate, in the presence of a base such as triethylamine, N,N-diisopropylethylamine or 4-dimethylaminopyridine, in a solvent such as dichloromethane, dichloroethane, N,N-dimethylformamide or tetrahydrofuran, at a temperature between –10° C. and the reflux temperature of the solvent.

As a functional derivative of the acid (III) it is possible to use the acid chloride, the anhydride, a mixed anhydride, a $C_1$-$C_4$ alkylester in which the alkyl is straight or branched, or an activated ester, for example the p-nitrophenyl ester.

Therefore, in the process according to the invention, it is also possible to react the acid chloride obtained by reacting thionyl chloride or oxalyl chloride with the acid of formula (III), with the compound of formula (II), in a solvent, such as a chlorinated solvent (dichloromethane, dichloroethane or chloroform, for example), an ether (tetrahydrofuran or dioxane, for example) or an amide (N,N-dimethylformamide, for example) under an inert atmosphere, at a temperature between 0° C. and the ambient temperature, in the presence of a tertiary amine such as triethylamine, N-methylmorpholine or pyridine.

One variant involves preparing the mixed anhydride of the acid of formula (III) by reacting ethyl chloroformate with the acid of formula (III) in the presence of a base such as triethylamine, and in reacting said mixed anhydride with the compound of formula (II), in a solvent such as dichloromethane, under an inert atmosphere, at the ambient temperature, in the presence of a base such as triethylamine.

When a compound of formula (II) is treated with an isothiocyanate of formula (VII), this operation is carried out in the presence of a base such as triethylamine, in a solvent such as dichloromethane and at a temperature between the ambient temperature and the reflux temperature of the solvent.

When a compound of formula (II) is treated with a sulfamoyl chloride of formula (XVII), the operation is carried out in the presence of a base such as triethylamine, in a solvent such as dichloromethane and at a temperature between 0° C. and the ambient temperature.

According to another variant of the process, a compound of formula (I) in which $R_2$ represents a ($C_1$-$C_3$)alkyl may be prepared by reacting a compound of formula (I) in which $R_2$=H with a ($C_1$-$C_3$)alkyl halide, in the presence of a base such as sodium hydride, in a solvent such as N,N-dimethylformamide and at a temperature between the ambient temperature and the reflux temperature of the solvent.

The compounds of formula (I) thus obtained may be subsequently separated from the reaction medium and purified in accordance with conventional methods, as for example by crystallization or chromatography.

The compounds of formula (II) are prepared by reacting a compound of formula:

(X)

in which $R_3$ and $R_4$ are as defined for a compound of formula (I) and Y represents a leaving group as defined above, preferably a halogen atom or an activated hydroxyl group such as a methanesulfonate, benzenesulfonate, p-toluenesulfonate or triflate group, with a compound of formula:

H$_2$N—$R_2$ (XI)

in which $R_2$ is as defined for a compound of formula (I).

The reaction is performed in a solvent such as N,N-dimethylformamide, acetonitrile, dichloromethane, toluene or propan-2-ol, and in the presence or absence of a base. When a base is used, it is selected from organic bases such as triethylamine, N,N-diisopropyl-ethylamine or N-methylmorpholine. The reaction is performed at a temperature between 0° C. and the reflux temperature of the solvent.

According to one variant, it is also possible to prepare a compound of formula (II) in which $R_2$=H by reacting a compound of formula (X) in which Y=Cl with 1,3,5,7-tetraazatricyclo[3.3.1$^{3,7}$]decane (or hexamethylenetetramine) in the presence of an alkali metal halide such as sodium iodide, in a solvent such as ethanol, at a temperature between the ambient temperature and the reflux temperature of the solvent, followed by hydrolysis with a strong acid such as hydrochloric acid.

According to another variant, finally, it is also possible to prepare a compound of formula (II) in which $R_2$=H by reacting a compound of formula:

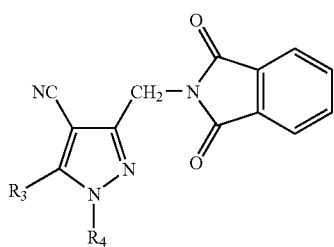

(XII)

in which $R_3$ and $R_4$ are as defined for a compound of formula (I) with hydrazine hydrate in a solvent such as methanol or ethanol and at a temperature between the ambient temperature and the reflux temperature of the solvent.

The compounds of the formula (III) are known or are prepared in accordance with known methods.

The compounds of formula (VII), (VIII) and (IX) are known or are prepared in accordance with known methods.

The compounds of formula (X) are prepared from compounds of formula:

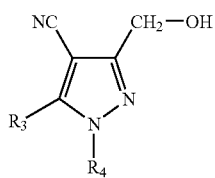

(XIII)

in which $R_3$ and $R_4$ are as defined for a compound of formula (I), in accordance with conventional methods.

Thus, for example, when Y in a compound of formula (X) represents a halogen atom, a compound of formula (XIII) is treated with a halogenating agent such as $PCl_5$, $PBr_3$, HBr, $BBr_3$ or $SOCl_2$ in a solvent such as dichloromethane or toluene and at a temperature between 0° C. and the reflux temperature of the solvent.

When Y in a compound of formula (X) represents a methanesulfonate, a benzenesulfonate, a p-toluene-sulfonate or a trifluoromethanesulfonate, a compound of formula (XIII) is reacted with a sulfonyl chloride of formula W—$SO_2$—Cl in which W represents a methyl, phenyl, p-tolyl or a trifluoromethyl. The reaction is performed in the presence of a base such as triethylamine, pyridine or N,N-diisopropylethylamine in a solvent such as dichloromethane or toluene and at a temperature between −20° C. and the reflux temperature of the solvent.

The compounds of formula (XI) are known.

The compounds of formula (XII) are prepared by reacting a compound of formula (X) in which Y=Cl with potassium phthalimide, in the presence of sodium iodide, in a solvent such as N,N-dimethylformamide and at a temperature between the ambient temperature and the reflux temperature of the solvent.

The compounds of formula (XIII) are prepared by reducing compounds of formula:

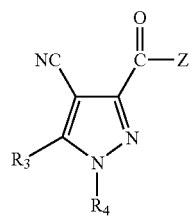

(XIV)

in which $R_3$ and $R_4$ are as defined for a compound of formula (I) and Z represents a ($C_1$-$C_2$)alkoxy.

The reaction is performed in the presence of a reducing agent such as sodium borohydride, potassium borohydride or lithium aluminum hydride, in the presence of lithium chloride, in a solvent such as tetrahydrofuran, and at a temperature of between the ambient temperature and the reflux temperature of the solvent.

The compounds of formula (XIV) are known or are prepared in accordance with the methods described in WO 2005/000 820.

Thus, for example, the compounds of formula (XIV) are prepared by reacting a compound of formula:

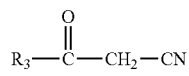

(XV)

in which $R_3$ is as defined for a compound of formula (I) with a compound of formula:

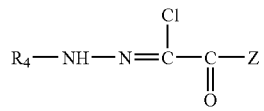

(XVI)

in which $R_4$ is as defined for a compound of formula (I) and Z represents a ($C_1$-$C_2$)alkoxy, in the presence of a base such as sodium ethoxide in a solvent such as ethanol, and at a temperature between the ambient temperature and the reflux temperature of the solvent.

The compounds of formula (XV) are known, available commercially or prepared in accordance with known methods.

The compounds of formula (XVI) are known or are prepared in accordance with the methods described in WO 2005/000 820.

The compounds of formula (XVII) are known or are prepared in accordance with known methods such as those described in J. Med. Chem., 1972, 15(5), 538-541; J. Chem. Soc. Perkin Trans 1, 1975, 2413-2416; J. Med. Chem., 1999, 42(7), 1178-1192; Helv. Chim. Acta., 1999, 82(12), 2432-2447; Bioorg. Med. Chem., 2005, 13, 1393-1402.

The EXAMPLES below describe the preparation of certain compounds in accordance with the invention. These examples are not limitative, and merely illustrate the present invention. The numbers of the compounds exemplified refer to those given in TABLE VI hereinafter, which illustrates the chemical structures and the physical properties of some compounds according to the invention.

In the Preparations and in the Examples, the abbreviations used are as follows:
ether: diethyl ether
iso ether: diisopropyl ether
DMSO: dimethyl sulfoxide
DMF: N,N-dimethylformamide
THF: tetrahydrofuran
PyBOP: benzotriazol-1-yloxytris(pyrrolidino)phosphonium hexafluorophosphate
DCM: dichloromethane
AcOEt: ethyl acetate
DIPEA: diisopropylethylamine
DBU: 1,8-diazabicyclo[5.4.0]undec-7-ene
TFA: trifluoroacetic acid
2N hydrochloric ether: 2N solution of hydrochloric acid in diethyl ether
m.p.: melting point
AT: ambient temperature
b.p.: boiling temperature
HPLC: high-performance liquid chromatography
Silica H: silica gel 60 H, sold by Merck (DARMSTADT)
Buffer solution pH=2: solution of 16.66 g of $KHSO_4$ and 32.32 g of $K_2SO_4$ in 1 liter of water.

The proton nuclear magnetic resonance ($^1H$ NMR) spectra are recorded in DMSO-$d_6$. The chemical shifts δ are expressed in parts per million (ppm). For the interpretation of the spectra, the following abbreviations are used: s: singlet, d: doublet, t: triplet, q: quadruplet, up: unresolved peak, mt: multiplet, bs: broad singlet, dd: divided doublet.

The compounds according to the invention are analyzed by LC/UV/MS coupling (liquid chromatography/UV detection/mass spectrometry). Measurements are made of the molecular peak ($MH^+$) and the retention time (tr) in minutes.

Method 1: M1
A Symmetry C18 column of 2.1×50 mm, 3.5 μm, is used at 30° C., flow rate 0.4 ml/minute.
The eluent is composed as follows:
solvent A: 0.005% of trifluoroacetic acid (TFA) in water at pH 3.15;
solvent B: 0.005% of TFA in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

UV detection is performed at λ=210 nm and mass detection is performed in positive ESI chemical ionization mode, to observe the ions obtained from the protonation of the compounds under analysis ($MH^+$).

Method 2: MS 2
An XTerra MS C18 column of 2.1×30 mm, 3.5 μm, is used at 30° C., flow rate 0.8 ml/minute.
The eluent is composed as follows:
solvent A: 0.025% of TFA in water;
solvent B: 0.025% of TFA in acetonitrile.
Gradient:

| Time (min) | % A | % B |
|---|---|---|
| 0 | 100 | 0 |
| 2 | 0 | 100 |
| 2.7 | 0 | 100 |
| 2.75 | 100 | 0 |

UV detection is performed by a diode array detector between 210 and 400 nm and mass detection is performed in positive ESI chemical ionization mode.

Method 3: MS 5
An XTerra MS C18 column of 2.1×30 mm, 3.5 μm, is used at 30° C., flow rate 1 ml/minute.
The eluent is composed as follows:
solvent A: 0.025% of trifluoroacetic acid (TFA) in water;
solvent B: 0.025% of TFA in acetonitrile.
Gradient:

| Time (min) | % A | % B |
|---|---|---|
| 0 | 100 | 0 |
| 2.0 | 0 | 100 |
| 2.7 | 0 | 100 |
| 2.75 | 100 | 0 |

UV detection is performed by a diode array detector between 210 and 400 nm and mass detection is performed in positive ESI chemical ionization mode.

Method 4: M2
An XTerra MS C18 column of 2×100 mm, 3.5 μm, is used at 30° C., flow rate 0.4 ml/minute.
The eluent is composed as follows:
solvent A: $AcONH_4$ 10 nM at pH=7;
solvent B: acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

UV detection is performed at λ=220 nm and mass detection is performed in positive ESI chemical ionization mode, to observe the ions obtained from the protonation of the compounds under analysis ($MH^+$).

Method 5: M 3
A Symmetry C18 column of 2.1×50 mm, 3.5 μm, is used at 30° C., flow rate 0.4 ml/minute.
The eluent is composed as follows:
solvent A: 0.005% of TFA in water at pH 3.1;
solvent B: 0.005% of TFA in acetonitrile.

Gradient:

| Time (min) | % A | % B |
|---|---|---|
| 0 | 100 | 0 |
| 20 | 10 | 90 |
| 30 | 10 | 90 |
| 35 | 100 | 0 |
| 40 | 100 | 0 |

UV detection is performed at λ=210-220 nm and mass detection is performed in positive ESI chemical electrospray mode, so as to observe the ions obtained from the protonation of the compounds under analysis (MH$^+$).

PREPARATIONS

1. Preparations of Compounds of Formula (XVI)

Preparation 1.1

Ethyl 2-chloro-[2,4-dichlorophenyl)hydrazono]acetate (XVI):

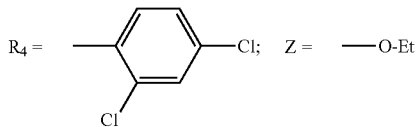

This compound is prepared in accordance with the procedure described in step A of Preparation 1 in WO 2005/000 820.

Preparation 1.2

Ethyl 2-chloro[(2-chlorophenyl)hydrazono]acetate (XVI):

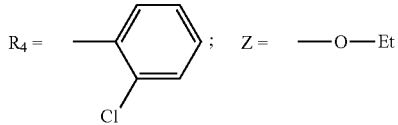

A solution of 25 g of 2-chloroaniline in 200 ml of a 24% strength HCl solution and 400 ml of water is cooled to 5° C. and a solution of 13.5 g of sodium nitride in 60 ml of water is added dropwise. This resultant diazonium salt solution is added to a mixture of 32.2 g of ethyl 2-chloro-3-oxobutanoate and 16.1 g of sodium acetate in 750 ml of EtOH, cooled to 5° C. beforehand, and then left for 2 hours 30 minutes with stirring, during which the temperature is allowed to rise to ambient temperature. The precipitate formed is filtered off with suction, washed with water and dried. This gives 49 g of the expected compound.

Preparation 1.3

Ethyl [(2-bromophenyl)hydrazono](chloro)acetate (XVI):

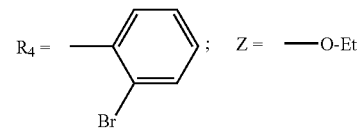

A solution of 25 g of 2-bromoaniline in 200 ml of a 24% strength HCl solution and 400 ml of water is cooled to 5° C. and a solution of 10 g of sodium nitride in 60 ml of water is added dropwise. This resultant diazonium salt solution is added to a mixture of 24 g of ethyl 2-chloro-3-oxobutanoate and 11.9 g of sodium acetate in 750 ml of EtOH, cooled to 5° C. beforehand, and then left for 2 hours 30 minutes with stirring, during which the temperature is allowed to rise to ambient temperature. The precipitate formed is filtered off with suction, washed with water and dried. This gives 34.7 g of the expected compound, m.p.=106° C.

2. Preparations of Compounds of the Formula (XIV)

Preparation 2.1

Ethyl 5-(4-chlorophenyl)-4-cyano-1-(2,4-dichlorophenyl)-1H-pyrazole-3-carboxylate (XIV):

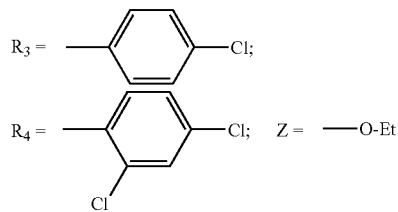

This compound is prepared by the procedure described in step B of Preparation 1 in WO 2005/000 820.

Preparation 2.2

Ethyl 4-cyano-1-(2,4-dichlorophenyl)-5-(4-methoxyphenyl)-1H-pyrazole-3-carboxylate (XIV):

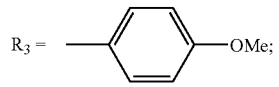

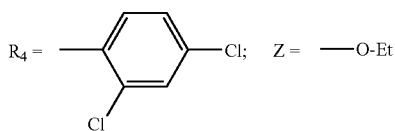

1.71 g of sodium are added in small portions and at ambient temperature to 350 ml of EtOH. Then a solution of 11.85 g of 3-(4-methoxyphenyl)-3-oxopropanenitrile in 500 ml of EtOH is added dropwise and at ambient temperature and the mixture is left with stirring at ambient temperature for 30 minutes. Finally, in small portions, 20 g of the compound from Preparation 1.1 are added and the mixture is left with stirring at ambient temperature for 48 hours. An insoluble material is removed by filtration and the filtrate is concentrated under vacuum. The residue is extracted with AcOEt, the organic phase is washed with saturated NaCl solution and dried over $MgSO_4$, and the solvent is evaporated under vacuum. The residue is chromatographed on silica gel, eluting with a cyclohexane/AcOEt (80/20; v/v) mixture. This gives 7 g of the expected compound.

Following the procedures described in Preparations 2, the compounds of formula (XIV) compiled in Table I below are prepared:

TABLE 1

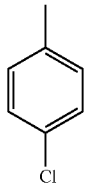

| Preparations | $R_3$ | $R_4$ |
|---|---|---|
| 2.3 | 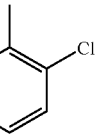 | 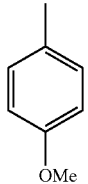 |
| 2.4 | 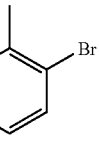 | 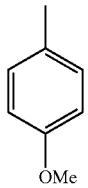 |
| 2.5 | 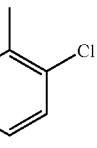 | 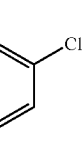 |

3. Preparations of Compounds of Formula (XIII)

Preparation 3.1

5-(4-Chlorophenyl)-1-(2,4-dichlorophenyl)-3-(hydroxymethyl)-1H-pyrazole-4-carbonitrile (XIII):

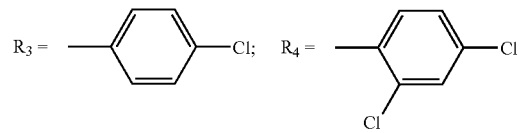

A solution of 7.6 g of the compound from Preparation 2.1 in 100 ml of THF is admixed with 1.17 g of potassium borohydride and 1 g of lithium chloride and then heated at reflux overnight. An insoluble material is removed by filtration and the filtrate is evaporated under vacuum. The residue is extracted with AcOEt, the organic phase is washed with water and with saturated NaCl solution and dried over $MgSO_4$, and the solvent is evaporated under vacuum. The residue is chromatographed on silica gel, eluting with a gradient of the cyclohexane/AcOEt mixture from (90/10; v/v) to (70/30; v/v). This gives 5.0 g of the expected compound following recrystallization from ether.

Following the procedures described in Preparation 3.1, the compounds of formula (XIII) compiled in Table II below are prepared:

TABLE II

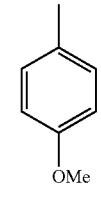

| Preparations | $R_3$ | $R_4$ |
|---|---|---|
| 3.2 | 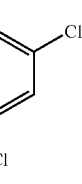 | 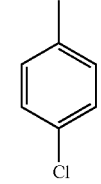 |
| 3.3 | 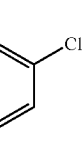 | 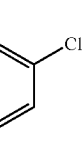 |

TABLE II-continued

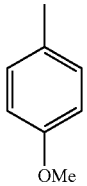
(XIII)

| Preparations | R₃ | R₄ |
|---|---|---|
| 3.4 | 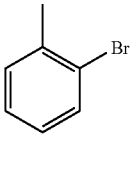 (4-OMe-phenyl) | 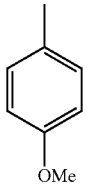 (2-Br-phenyl) |
| 3.5 | 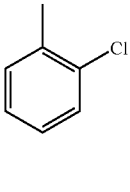 (4-OMe-phenyl) | 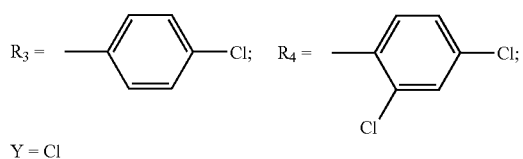 (2-Cl-phenyl) |

4. Preparations of Compounds of Formula (X)

Preparation 4.1

3-(Chloromethyl)-5-(4-chlorophenyl)-1-(2,4-dichlorophenyl)-1H-pyrazole-4-carbonitrile (X):

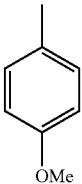

$R_3$ = 4-Cl-phenyl; $R_4$ = 2,4-diCl-phenyl; Y = Cl

A solution of 6 g of the compound from Preparation 3.1 in 40 ml of DCM is cooled to 0° C. and then admixed in small fractions with 4.3 g of PCl₅ and left for 2 hours with stirring, during which the temperature is allowed to return to ambient temperature. The reaction mixture is poured into 50 ml of water, the phases are separated, the organic phase is washed with saturated NaCl solution and dried over MgSO₄ and the solvent is evaporated under vacuum. This gives 6.4 g of the expected compound, following recrystallization from an ether/iso ether mixture.

Following the procedure described in Preparation 4.1, the compounds of formula (X) compiled in Table III below are prepared:

TABLE III

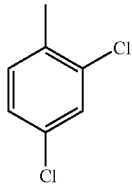
(X)

| Preparations | R₃ | R₄ | Y |
|---|---|---|---|
| 4.2 | 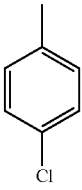 (4-OMe-phenyl) | 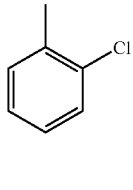 (2,4-diCl-phenyl) | Cl |
| 4.3 | 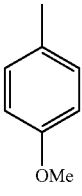 (4-Cl-phenyl) | 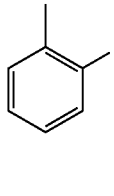 (2-Cl-phenyl) | Cl |
| 4.4 | 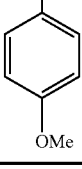 (4-OMe-phenyl) | 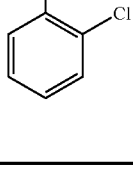 (2-Br-phenyl) | Cl |
| 4.5 | 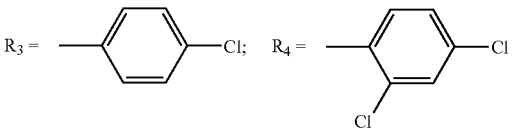 (4-OMe-phenyl) | (2-Cl-phenyl) | Cl |

5. Preparations of Compounds of Formula (XII)

Preparation 5.1

5-(4-Chlorophenyl)-1-(2,4-dichlorophenyl)-3-[(1,3-dioxo-1,3-dihydro-2H-isoindol-2-yl)methyl-1H-pyrazole-4-carbonitrile (XII):

$R_3$ = 4-Cl-phenyl; $R_4$ = 2,4-diCl-phenyl

A solution of 6.3 g of the compound from Preparation 4.1 in 50 ml of DMF is admixed with 3.5 g of potassium phthalimide and 2.85 g of NaI and then heated at 65° C. for 1 hour. The reaction mixture is concentrated under vacuum, the residue is extracted with AcOEt, the organic phase is washed with saturated NaCl solution and dried over MgSO₄ and the solvent is evaporated under vacuum. This gives 7.8 g of the expected compound.

Following the procedure described in Preparation 5.1, the compounds of formula (XII) compiled in Table IV below are prepared:

TABLE IV (XII)

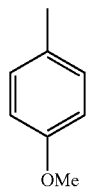

| Preparations | R$_3$ | R$_4$ |
|---|---|---|
| 5.2 | 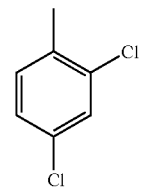 | 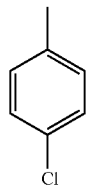 |
| 5.3 | 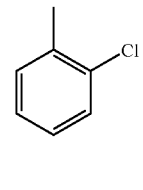 | 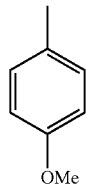 |
| 5.4 | 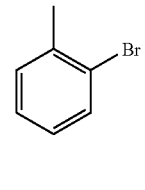 | 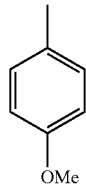 |
| 5.5 | 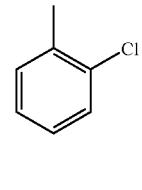 | 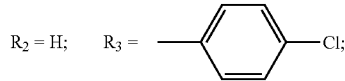 |

6. Preparations of Compounds of Formula (II)
Preparation 6.1

3-(Aminomethyl)-5-(4-chlorophenyl)-1-(2,4-dichlorophenyl)-1H-pyrazole-4-carbonitrile (II):

R$_2$ = H;  R$_3$ = 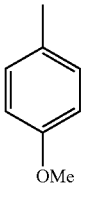;

R$_4$ = 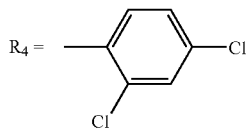

A solution of 7.8 g of the compound from Preparation 5.1 in 100 ml of EtOH is admixed with 1.61 g of hydrazine hydrate and heated at reflux for 1 hour. An insoluble material is removed by filtration and the filtrate is evaporated under vacuum. The residue is extracted with AcOEt, the organic phase is washed with saturated NaCl solution and dried over MgSO$_4$ and the solvent is evaporated under vacuum. This gives 5.7 g of the expected compound.

Following the procedure described in Preparation 6.1, the compounds of formula (II) compiled in Table V below are prepared:

TABLE V

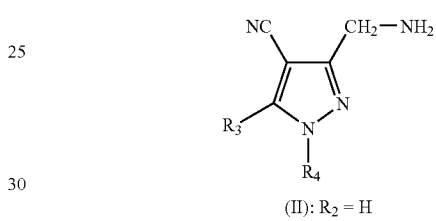

(II): R$_2$ = H

| Preparations | R$_3$ | R$_4$ |
|---|---|---|
| 6.2 | 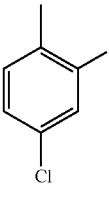 | 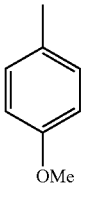 |
| 6.3 | 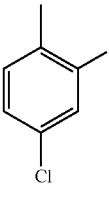 | 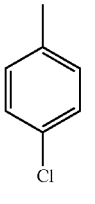 |
| 6.4 | 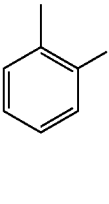 | 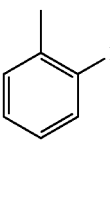 |

TABLE V-continued

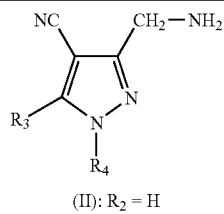

(II): $R_2 = H$

| Preparations | $R_3$ | $R_4$ |
|---|---|---|
| 6.5 | 4-OMe-phenyl | 2-Cl-phenyl |

Example 1

Compound 16

N-[[5-(4-Chlorophenyl)-4-cyano-1-(2,4-dichlorophenyl)-1H-pyrazol-3-yl]methyl]-4-(trifluoromethoxy)benzamide A solution of 0.24 g of 4-(trifluoromethoxy)benzoic acid in 25 ml of DCM is admixed successively with 1.1 g of PyBOP, 0.32 ml of triethylamine and 0.4 g of the compound from Preparation 6.1, and then left for 2 hours with stirring at ambient temperature. Then 15 ml of water are added and the mixture is left for 10 minutes with stirring, the phases are separated, the organic phase is washed with a buffer solution pH=2, with saturated NaHCO$_3$ solution, and with saturated NaCl solution and dried over MgSO$_4$ and the solvent is evaporated under vacuum. The residue is chromatographed on silica gel, eluting with a gradient of the cyclohexane/AcOEt mixture from (90/10; v/v) to (80/20; v/v). This gives 0.414 g after recrystallization from a DCM/iso ether mixture, m.p.=180° C.

Example 2

Compound 19

N-[[5-(4-Chlorophenyl)-4-cyano-1-(2,4-dichlorophenyl)-1H-pyrazol-3-yl]methyl]-4-(1H-pyrrol-1-yl)benzamide A solution of 0.22 g of 4-(1H-pyrrol-1-yl)benzoic acid in 21 ml of DCM is admixed successively with 1.1 g of PyBOP, 0.32 ml of triethylamine and 0.4 g of the compound from Preparation 6.1, and then left overnight with stirring at ambient temperature. Then 10 ml of water are added and the mixture is left for 10 minutes with stirring, the phases are separated, the organic phase is washed with a buffer solution pH=2, with saturated NaHCO$_3$ solution, and with saturated NaCl solution and dried over MgSO$_4$ and the solvent is evaporated under vacuum. The residue is chromatographed on silica gel, eluting with DCM. This gives 0.19 g of the expected compound, m.p.=121° C.

Example 3

Compound 27

1-[[5-(4-Chlorophenyl)-4-cyano-1-(2,4-dichlorophenyl)-1H-pyrazol-3-yl]methyl]-3-(3-methoxyphenyl)thiourea A solution of 0.4 g of the compound from Preparation 6.1 in 20 ml of 20 DCM is admixed with 0.16 ml of triethylamine and 0.2 g of 3-methoxyphenyl isothiocyanate and then left overnight with stirring at ambient temperature. Then 10 ml of water are added and the mixture is left for 10 minutes with stirring, the phases are separated, the organic phase is washed with saturated NaCl solution, and the solvent is evaporated under vacuum. The residue is extracted with AcOEt, the organic phase is washed with a buffer solution pH=2, with saturated NaHCO$_3$ solution, and with saturated NaCl solution and dried over MgSO$_4$, and the solvent is evaporated under vacuum. The residue is chromatographed from silica gel, eluting with a cyclohexane/AcOEt mixture (90/10; v/v). This gives 0.41 g of the expected compound, m.p. =162° C.

Example 4

Compound 82

N-[[1-(2-Chlorophenyl)-5-(4-chlorophenyl)-4-cyano-1H-pyrazol-3-yl]methyl]-4-cyanobenzamide A suspension of 0.19 g of 4-cyanobenzoic acid in 23 ml of DCM is admixed with 1.33 g of PyBOP and then 0.4 g of the compound from Preparation 6.3 and 0.36 ml of triethylamine and is left overnight with stirring at ambient temperature. Then 10 ml of water are added and the mixture is left for 10 minutes with stirring, the phases are separated, and the organic phase is concentrated under vacuum. The residue is extracted with AcOEt, the organic phase is washed with saturated NaHCO$_3$ solution, with a buffer solution pH=2, and with saturated NaCl solution and dried over MgSO$_4$, and the solvent is evaporated under vacuum. The residue is chromatographed from silica gel, eluting with a gradient of the cyclohexane/AcOEt mixture from (98/2; v/v) to (90/10; v/v). This gives 0.29 g of the expected compound following recrystallization from iso ether, m.p.=118° C.

Example 5

Compound 60

N-[[1-(2-Chlorophenyl)-5-(4-chlorophenyl)-4-cyano-1H-pyrazol-3-yl]methyl]-1-[(4-chlorophenyl)sulfonyl]cyclopentanecarboxamide.

A suspension of 0.37 g of 1-[(4-chlorophenyl)sulfonyl]-cyclopentanecarboxylic acid in 24 ml of DCM is admixed with 1.23 g of PyBOP and then 0.36 ml of triethylamine and 0.45 g of the compound from Preparation 6.3 and is left overnight with stirring at ambient temperature. Then 10 ml of water are added and the mixture is left for 10 minutes with stirring, the phases are separated, the organic phase is washed with a buffer solution pH=2, and with saturated NaCl solution and dried over MgSO$_4$, and the solvent is evaporated under vacuum. The residue is chromatographed from silica gel, eluting with a gradient of the cyclohexane/AcOEt mixture from (98/2; v/v) to (80/20; v/v). This gives 0.56 g of the expected compound, m.p.=109° C.

The table which follows illustrates the chemical structures and the physical properties of some examples of compounds according to the invention.

In this table:

Me, Et, Pr, n-Bu and t-Bu represent methyl, ethyl, propyl, n-butyl, and tert-butyl, respectively.

TABLE VI

Structure (I): R₂ = H, with substituents NC, CH₂—NH—X—R₁, R₃, R₄ on pyrazole ring.

| Compound No. | —X— | R₁ | R₃ | R₄ | MH⁺; tr (min) Method NMR |
|---|---|---|---|---|---|
| 1 | —CO— | t-Bu | 4-Cl-phenyl | 2,4-diCl-phenyl | 460.8; 1.96 MS 5 |
| 2 | —CO— | —CH(Et)₂ | 4-Cl-phenyl | 2,4-diCl-phenyl | 474.9; 1.99 MS 5 |
| 3 | —CO— | —CH(nPr)₂ | 4-Cl-phenyl | 2,4-diCl-phenyl | 503; 10.85 M 1 |
| 4 | —CO— | —CH₂—CH(Ph)₂ | 4-Cl-phenyl | 2,4-diCl-phenyl | 585; 11.5 M 1 NMR |
| 5 | —CO— | —C(Me)₂—O—(2-Cl-phenyl) | 4-Cl-phenyl | 2,4-diCl-phenyl | 572.8; 2.21 MS 5 |
| 6 | —CO— | —C(Me)₂—O—(4-Cl-phenyl) | 4-Cl-phenyl | 2,4-diCl-phenyl | 572.8; 2.24 MS 5 |

TABLE VI-continued (I): R₂ = H

| Compound No. | —X— | R₁ | R₃ | R₄ | MH⁺; tr (min) Method NMR |
|---|---|---|---|---|---|
| 7 | —CO— | Me₂C(—)—O—(3-CF₃-phenyl) | 4-Cl-phenyl | 2,4-diCl-phenyl | 607; 12.06 M 1 |
| 8 | —CO— | Me₂C(—)—O—(5-CF₃-pyridin-2-yl) | 4-Cl-phenyl | 2,4-diCl-phenyl | 608; 11.79 M 1 |
| 9 | —CO— | cyclopentyl | 4-Cl-phenyl | 2,4-diCl-phenyl | 472.9; 2 MS 5 |
| 10 | —CO— | cyclohexyl | 4-Cl-phenyl | 2,4-diCl-phenyl | 486.9; 2.07 MS 5 |
| 11 | —CO— | 1-methylcyclohexyl | 4-Cl-phenyl | 2,4-diCl-phenyl | 500.9; 2.09 MS 5 |
| 12 | —CO— | cycloheptyl | 4-Cl-phenyl | 2,4-diCl-phenyl | 500.9; 2.07 MS 5 |

TABLE VI-continued
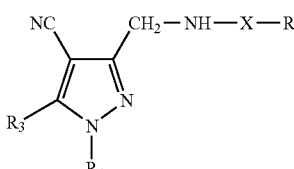
(I): $R_2 = H$
| Compound No. | —X— | $R_1$ | $R_3$ | $R_4$ | $MH^+$; tr (min) Method NMR |
|---|---|---|---|---|---|
| 13 | —CO— | 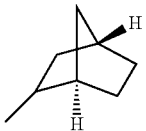 | 4-Cl-C6H4 | 2,4-diCl-C6H3 | 498.8; 2.09 MS 5 |
| 14 | —CO— | 3,5-diMe-C6H3 | 4-Cl-C6H4 | 2,4-diCl-C6H3 | 508.8; 2.09 MS 5 |
| 15 | —CO— | 4-tBu-C6H4 | 4-Cl-C6H4 | 2,4-diCl-C6H3 | 537; 11.89 M 1 |
| 16 | —CO— | 4-OCF3-C6H4 | 4-Cl-C6H4 | 2,4-diCl-C6H3 | 565; 11.51 M 1 |
| 17 | —CO— | 5-(2,3-dihydrobenzofuran) | 4-Cl-C6H4 | 2,4-diCl-C6H3 | 522.8; 2.01 MS 5 |
| 18 | —CO— | 4-phenoxy-C6H4 | 4-Cl-C6H4 | 2,4-diCl-C6H3 | 572.8; 2.16 MS 5 |

TABLE VI-continued
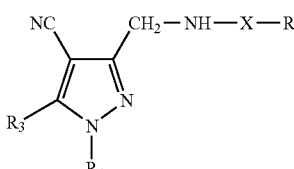
(I): R₂ = H
| Compound No. | —X— | R₁ | R₃ | R₄ | MH⁺; tr (min) Method NMR |
|---|---|---|---|---|---|
| 19 | —CO— | 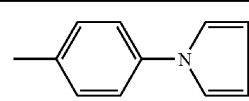 | 4-Cl-C₆H₄ | 2,4-Cl₂-C₆H₃ | 546; 11.1 M 1 NMR |
| 20 | —CO— | 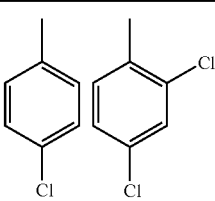 | 4-Cl-C₆H₄ | 2,4-Cl₂-C₆H₃ | 505.8; 2.01 MS 5 |
| 21 | —CO— | 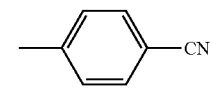 | 4-Cl-C₆H₄ | 2,4-Cl₂-C₆H₃ | 520.7; 2.06 MS 5 |
| 22 | —CO— | 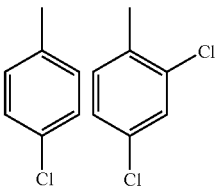 | 4-Cl-C₆H₄ | 2,4-Cl₂-C₆H₃ | 520; 10.74 M 1 |
| 23 | —CO— | 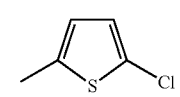 | 4-Cl-C₆H₄ | 2,4-Cl₂-C₆H₃ | 534; 18.16 M 3 |
| 24 | —CO— | 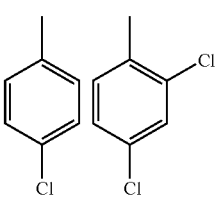 | 4-Cl-C₆H₄ | 2,4-Cl₂-C₆H₃ | 537.8; 1.91 MS 5 |

TABLE VI-continued
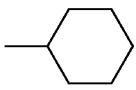
(I): R₂ = H
| Compound No. | —X— | R₁ | R₃ | R₄ | MH⁺; tr (min) Method NMR |
|---|---|---|---|---|---|
| 25 | —CSNH— | cyclohexyl-CH₂ | 4-Cl-C₆H₄ | 2,4-diCl-C₆H₃ | 517.9; 2.13 MS 5 |
| 26 | —CSNH— | 4-CF₃-C₆H₄-CH₂ | 4-Cl-C₆H₄ | 2,4-diCl-C₆H₃ | 579.8; 2.18 MS 5 |
| 27 | —CSNH— | 3-OMe-C₆H₄-CH₂ | 4-Cl-C₆H₄ | 2,4-diCl-C₆H₃ | 542; 10.95 M 1 NMR |
| 28 | —CSNH— | 3-(C(O)Me)-C₆H₄-CH₂ | 4-Cl-C₆H₄ | 2,4-diCl-C₆H₃ | 553.8; 2.04 MS 5 |
| 29 | —CSNH— | 4-CN-C₆H₄-CH₂ | 4-Cl-C₆H₄ | 2,4-diCl-C₆H₃ | 536.8; 2.03 MS 5 |
| 30 | —CO— | nBu | 4-OMe-C₆H₄ | 2,4-diCl-C₆H₃ | 456.9; 6.26 MS 5 |

TABLE VI-continued
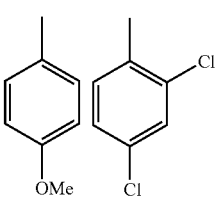
(I): R₂ = H
| Compound No. | —X— | R₁ | R₃ | R₄ | MH⁺; tr (min) Method NMR |
|---|---|---|---|---|---|
| 31 | —CO— | —CH(nPr)₂ | 4-OMe-C₆H₄ | 2,4-diCl-C₆H₃ | 498.9; 6.95 MS 5 |
| 32 | —CO— | cyclopentyl | 4-OMe-C₆H₄ | 2,4-diCl-C₆H₃ | 468.9; 6.27 MS 5 |
| 33 | —CO— | 4-OCF₃-C₆H₄ | 4-OMe-C₆H₄ | 2,4-diCl-C₆H₃ | 561; 10.86 M 1 |
| 34 | —CO— | 5-methyl-2,3-dihydrobenzofuran | 4-OMe-C₆H₄ | 2,4-diCl-C₆H₃ | 518.8; 6.33 MS 5 |
| 35 | —CO— | nBu | 4-Cl-C₆H₄ | 2-Cl-C₆H₄ | 427.6; 1.77 MS 2 |
| 36 | —CO— | tBu | 4-Cl-C₆H₄ | 2-Cl-C₆H₄ | 427.5; 1.77 MS 2 |

TABLE VI-continued (I): R₂ = H

| Compound No. | —X— | R₁ | R₃ | R₄ | MH⁺; tr (min) Method NMR |
|---|---|---|---|---|---|
| 37 | —CO— | —CH(Et)₂ | 4-Cl-phenyl | 2-Cl-phenyl | 441.6; 1.8 MS 2 |
| 38 | —CO— | —CH(nPr)₂ | 4-Cl-phenyl | 2-Cl-phenyl | 496.6; 1.91 MS 2 |
| 39 | —CO— | —CH₂-cyclopentyl | 4-Cl-phenyl | 2-Cl-phenyl | 453.6; 1.83 MS 2 |
| 40 | —CO— | —CH₂-cyclohexyl | 4-Cl-phenyl | 2-Cl-phenyl | 467.6; 1.88 MS 2 |
| 41 | —CO— | —CH(OMe)-phenyl | 4-Cl-phenyl | 2-Cl-phenyl | 491.6; 1.83 MS 2 |
| 42 | —CO— | —CH(phenyl)(CH₂-cyclohexyl) | 4-Cl-phenyl | 2-Cl-phenyl | 543.6; 2.02 MS 2 |

TABLE VI-continued
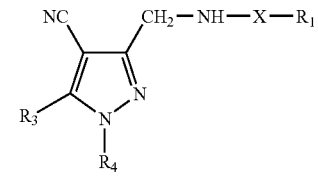
(I): R$_2$ = H
| Compound No. | —X— | R$_1$ | R$_3$ | R$_4$ | MH$^+$; tr (min) Method NMR |
|---|---|---|---|---|---|
| 43 | —CO— | 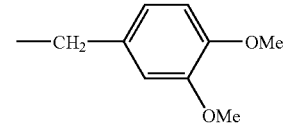 | 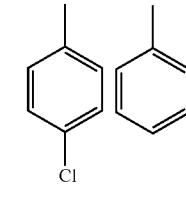 | 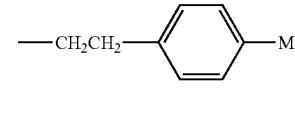 | 521.6; 1.72 MS 2 |
| 44 | —CO— | 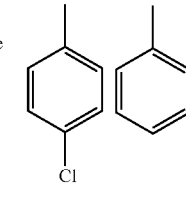 | 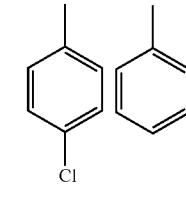 | 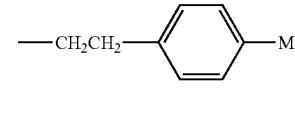 | 489.6; 1.87 MS 2 |
| 45 | —CO— | 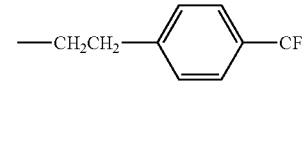 | 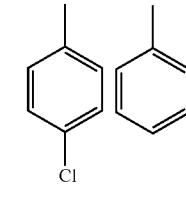 | 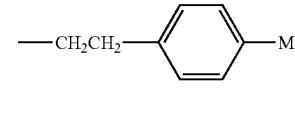 | 543; 10.96 M 1 NMR |
| 46 | —CO— | 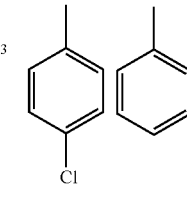 | 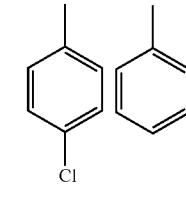 | 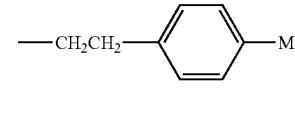 | 551; 11.14 M 1 NMR |
| 47 | —CO— | 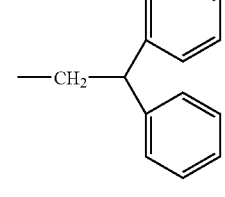 | 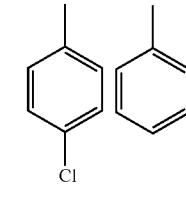 | 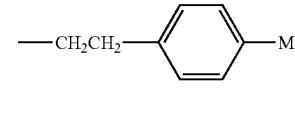 | 539; 11.19 M 1 NMR |
| 48 | —CO— | 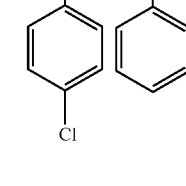 | 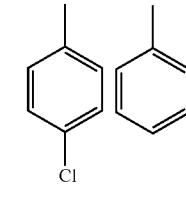 | 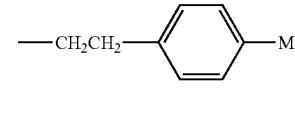 | 539.5; 1.97 MS 2 |

TABLE VI-continued
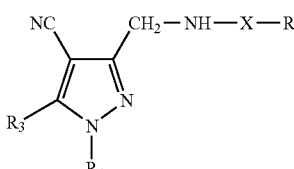
(I): R₂ = H
| Compound No. | —X— | R₁ | R₃ | R₄ | MH⁺; tr (min) Method NMR |
|---|---|---|---|---|---|
| 49 | —CO— | 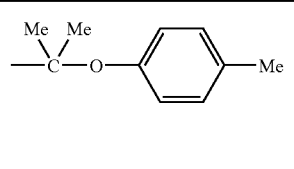 | 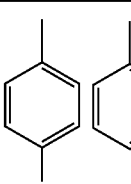 | 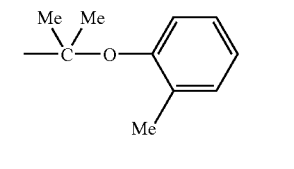 | 519; 11.27 M 1 |
| 50 | —CO— | 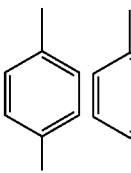 | 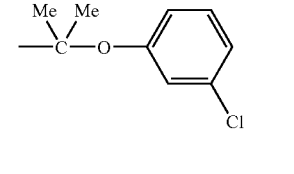 | 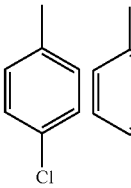 | 519; 11.07 M 2 NMR |
| 51 | —CO— | 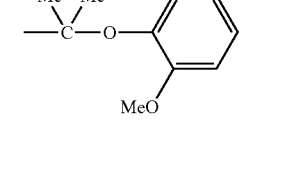 | 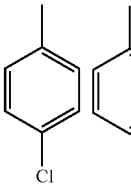 | 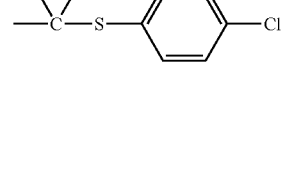 | 539; 11.28 M 1 |
| 52 | —CO— | 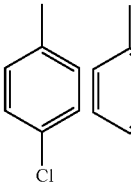 | | | 535; 10.86 M 1 |
| 53 | —CO— | 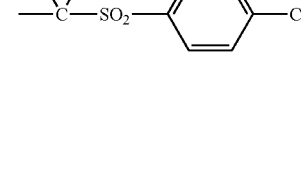 | | | 555; 11.37 M 1 |
| 54 | —CO— | 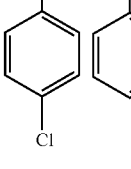 | | | 587; 10.97 M 1 |

TABLE VI-continued
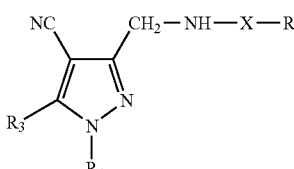
(I): $R_2$ = H
| Compound No. | —X— | $R_1$ | $R_3$ | $R_4$ | $MH^+$; tr (min) Method NMR |
|---|---|---|---|---|---|
| 55 | —CO— | 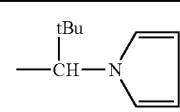 | 4-Cl-C6H4 | 2-Cl-C6H4 | 506.6; 1.95 MS 2 |
| 56 | —CO— | 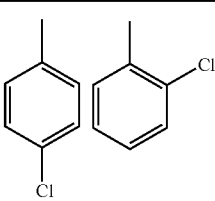 | 4-Cl-C6H4 | 2-Cl-C6H4 | 425.5; 1.74 MS 2 |
| 57 | —CO— | 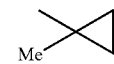 | 4-Cl-C6H4 | 2-Cl-C6H4 | 439.5; 1.78 MS 2 |
| 58 | —CO— | 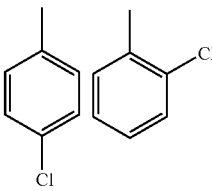 | 4-Cl-C6H4 | 2-Cl-C6H4 | 453.6; 1.82 MS 2 |
| 59 | —CO— | 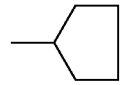 | 4-Cl-C6H4 | 2-Cl-C6H4 | 467.6; 1.89 MS 2 |
| 60 | —CO— | 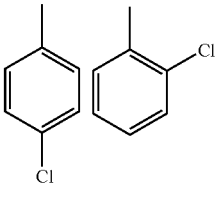 | 4-Cl-C6H4 | 2-Cl-C6H4 | 613; 11.46 M 1 NMR |

TABLE VI-continued
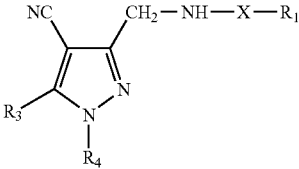
(I): R$_2$ = H
| Compound No. | —X— | R$_1$ | R$_3$ | R$_4$ | MH$^+$; tr (min) Method NMR |
|---|---|---|---|---|---|
| 61 | —CO— | 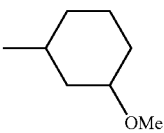 | 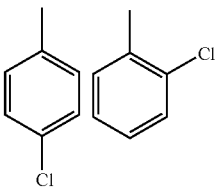 | 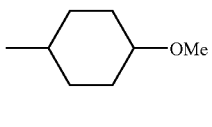 | 483.6; 1.73 MS 2 |
| 62 | —CO— | 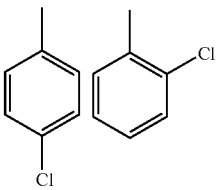 | 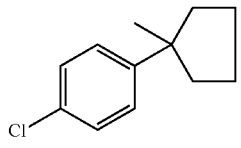 | 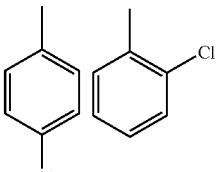 | 483.6; 1.71 MS 2 |
| 63 | —CO— | 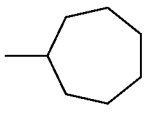 | | | 549.5; 2.02 MS 2 |
| 64 | —CO— | 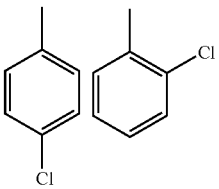 | | | 467.6; 1.88 MS 2 |
| 65 | —CO— | 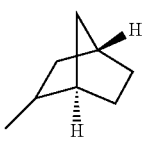 | | | 465.6; 1.86 MS 2 |
| 66 | —CO— | 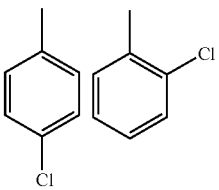 | | | 447.5; 1.77 MS 2 |

TABLE VI-continued

Structure (I): R₂ = H, with pyrazole core bearing NC, CH₂—NH—X—R₁, R₃, and N—R₄ substituents.

| Compound No. | —X— | R₁ | R₃ | R₄ | MH⁺; tr (min) Method NMR |
|---|---|---|---|---|---|
| 67 | —CO— | 3-Cl-phenyl | 4-Cl-phenyl | 2-Cl-phenyl | 481.5; 1.86 MS 2 |
| 68 | —CO— | 2-Cl-phenyl | 4-Cl-phenyl | 2-Cl-phenyl | 481.5; 1.8 MS 2 |
| 69 | —CO— | 2,6-diF-phenyl | 4-Cl-phenyl | 2-Cl-phenyl | 483.5; 1.78 MS 2 |
| 70 | —CO— | 3,5-diMe-phenyl | 4-Cl-phenyl | 2-Cl-phenyl | 475.6; 1.88 MS 2 |
| 71 | —CO— | 4-tBu-phenyl | 4-Cl-phenyl | 2-Cl-phenyl | 503.6; 1.95 MS 2 |
| 72 | —CO— | 3-OMe-phenyl | 4-Cl-phenyl | 2-Cl-phenyl | 477.5; 1.79 MS 2 |

TABLE VI-continued
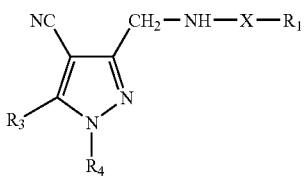
(I): R₂ = H
| Compound No. | —X— | R₁ | R₃ | R₄ | MH⁺; tr (min) Method NMR |
|---|---|---|---|---|---|
| 73 | —CO— | 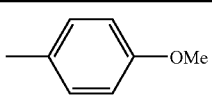 | 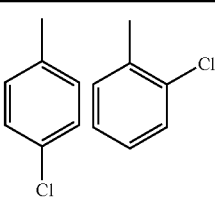 |  | 477.5; 1.78 MS 2 |
| 74 | —CO— | 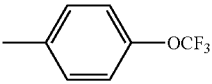 | 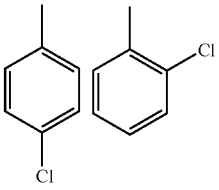 |  | 531; 10.92 M 1 NMR |
| 75 | —CO— | 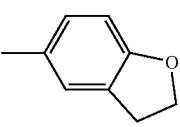 | 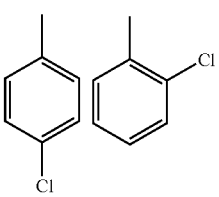 |  | 489.5; 1.78 MS 2 |
| 76 | —CO— | 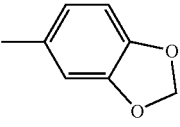 | 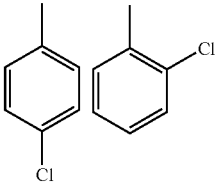 |  | 491.5; 1.78 MS 2 |
| 77 | —CO— | 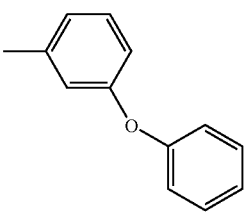 | 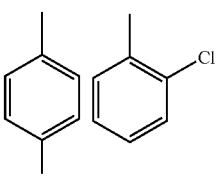 |  | 539.5; 1.95 MS 2 |
| 78 | —CO— | 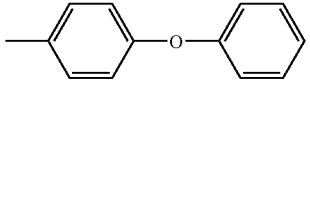 | 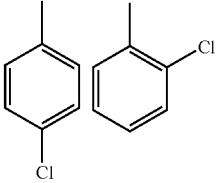 |  | 539.5; 1.94 MS 2 |

TABLE VI-continued (I): R$_2$ = H

| Compound No. | —X— | R$_1$ | R$_3$ | R$_4$ | MH$^+$; tr (min) Method NMR |
|---|---|---|---|---|---|
| 79 | —CO— | 3-methylphenyl-N(Me)$_2$ | 4-Cl-phenyl | 2-Cl-phenyl | 490.6; 1.62 MS 2 |
| 80 | —CO— | 4-methylphenyl-C(O)-Me | 4-Cl-phenyl | 2-Cl-phenyl | 489.5; 1.75 MS 2 |
| 81 | —CO— | 4-methylphenyl-C(O)-O-Me | 4-Cl-phenyl | 2-Cl-phenyl | 505.5; 1.8 MS 2 |
| 82 | —CO— | 4-methylphenyl-CN | 4-Cl-phenyl | 2-Cl-phenyl | 472; 9.79 M 1 NMR |
| 83 | —CO— | 4-methylphenyl-N-pyrrolyl | 4-Cl-phenyl | 2-Cl-phenyl | 512.5; 1.88 MS 2 |
| 84 | —CO— | 2,3-dimethyl-dihydropyran | 4-Cl-phenyl | 2-Cl-phenyl | 467.5; 1.75 MS 2 |

TABLE VI-continued
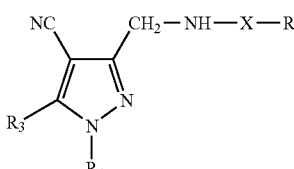
(I): R₂ = H
| Compound No. | —X— | R₁ | R₃ | R₄ | MH⁺; tr (min) Method NMR |
|---|---|---|---|---|---|
| 85 | —CO— | 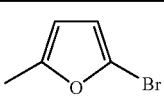 | 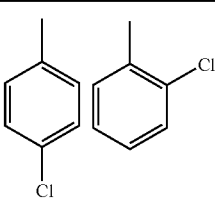 | 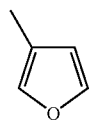 | 515.4; 1.81 MS 2 |
| 86 | —CO— | 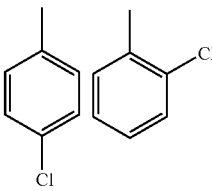 | 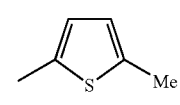 | 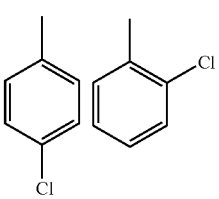 | 437.5; 1.71 MS 2 |
| 87 | —CO— | 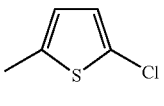 | | | 467.5; 1.81 MS 2 |
| 88 | —CO— | 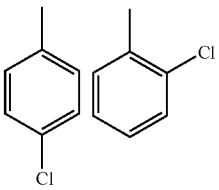 | | | 487.5; 1.87 MS 2 |
| 89 | —CO— | 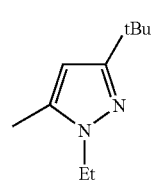 | 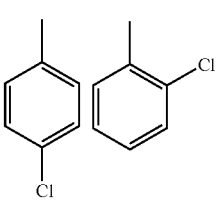 | | 521.6; 1.92 MS 2 |
| 90 | —CO— | 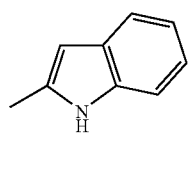 | 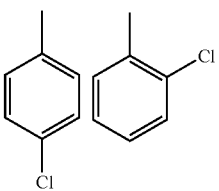 | | 486.5; 1.84 MS 2 |

TABLE VI-continued

| Compound No. | —X— | R₁ | R₃ | R₄ | MH⁺; tr (min) Method NMR |
|---|---|---|---|---|---|
| 91 | —CO— | 2-methyl-1-methyl-indol-3-yl | 4-Cl-phenyl | 2-Cl-phenyl | 500.6; 1.91 MS 2 |
| 92 | —CO— | 6-methyl-benzothiazol-2-yl | 4-Cl-phenyl | 2-Cl-phenyl | 504.5; 1.74 MS 2 |
| 93 | —CSNH— | methyl-cyclohexyl | 4-Cl-phenyl | 2-Cl-phenyl | 484.5; 1.89 MS 2 |
| 94 | —CSNH— | 3-methoxy-5-methyl-phenyl | 4-Cl-phenyl | 2-Cl-phenyl | 508.5; 1.84 MS 2 |
| 95 | —CSNH— | 3-acetyl-5-methyl-phenyl | 4-Cl-phenyl | 2-Cl-phenyl | 520.5; 1.8 MS 2 |
| 96 | —CO— | C(Me)₂-O-(2-Cl-phenyl) | 4-OMe-phenyl | 2-Br-phenyl | 579; 10.88 M 1 |

TABLE VI-continued
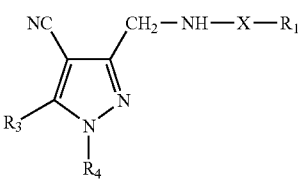
(I): $R_2$ = H
| Compound No. | —X— | $R_1$ | $R_3$ | $R_4$ | MH⁺; tr (min) Method NMR |
|---|---|---|---|---|---|
| 97 | —CO— | C(Me)(Me)—O—(3-Cl-phenyl) | 4-OMe-phenyl | 2-Br-phenyl | 579; 10.76 M 1 |
| 98 | —CO— | C(Me)(Me)—O—(3-OMe-phenyl) | 4-OMe-phenyl | 2-Br-phenyl | 575; 10.23 M 1 |
| 99 | —CO— | C(Me)(Me)—O—(3-Cl-phenyl) | 4-OMe-phenyl | 2-Cl-phenyl | 535; 10.9 M 1 NMR |
| 100 | —CO— | C(Me)(Me)—O—(2-Me-phenyl) | 4-OMe-phenyl | 2-Cl-phenyl | 515; 10.72 M 1 |
| 101 | —CO— | C(Me)(Me)—O—(4-Me-phenyl) | 4-OMe-phenyl | 2-Cl-phenyl | 515; 10.42 M 1 |
| 102 | —CO— | C(Me)(Me)—O—(3-CF₃-phenyl) | 4-OMe-phenyl | 2-Cl-phenyl | 569; 11.09 M 1 |

TABLE VI-continued (I): $R_2 = H$

| Compound No. | —X— | $R_1$ | $R_3$ | $R_4$ | MH$^+$; tr (min) Method NMR |
|---|---|---|---|---|---|
| 103 | —CO— | -⟨⟩-tBu | 4-OMe-phenyl | 2-Cl-phenyl | 499; 10.54 M 1 |

Compound 4: $^1$H NMR: DMSO-d$_6$ (400 MHz): δ (ppm): 2.96:d:2H; 4.40:d:2H; 4.54:t:1H; 7.10-7.18:up:2H; 7.20-7.30:up:8H; 7.33:d:2H; 7.57:d:2H; 7.65:dd:1H; 7.74:d:1H; 7.84:d:1H; 8.62:t:1H.

Compound 19: $^1$H NMR: DMSO-d$_6$ (250 MHz): δ (ppm): 4.92:d:2H; 6.52:t:2H; 7.57:d:2H; 7.71:t:2H; 7.77:d:2H; 7.81-7.88:dd:1H; 7.93:d:2H; 8.01:d:1H; 8.06:d:1H; 8.22:d:2H; 9.48:t:1H.

Compound 27: $^1$H NMR: DMSO-d$_6$ (250 MHz): δ (ppm): 3.65:s:3H; 4.95:s:2H; 6.66:mt:1H; 6.92:mt:1H; 7.09-726:up:2H; 7.33:d:2H; 7.53:d:2H; 7.60:mt:1H; 7.72-7.86:up:2H; 8.23:bp:1H; 9.82:bp:1H.

Compound 45: $^1$H NMR: DMSO-d$_6$ (400 MHz): δ (ppm): 2.49:mt:2H; 2.96:t:2H; 4.53:d:2H; 7.34:d:2H; 7.44:d:2H; 7.78-7.66:up:7H; 7.74:d:1H; 8.64:t:1H.

Compound 46: $^1$H NMR: DMSO-d$_6$ (400 MHz): δ (ppm): 2.99:d:2H; 4.40:d:2H; 4.54:t:1H 7.14:mt:2H; 7.18-7.29:up:8H; 7.32:d:2H; 7.49-7.65:up:5H; 7.69:d:1H; 8.65:t:1H.

Compound 47: $^1$H NMR: DMSO-d$_6$(400 MHz): δ (ppm): 1.48:s:6H; 4.57:d:2H; 6.95-7.06:up:2H; 7.14:mt:1H; 7.35:d:2H; 7.44:mt:1H; 7.50-7.66:up:5H; 7.72:mt:1H; 8.87:t:1H.

Compound 50: $^1$H NMR: DMSO-d$_6$ (250 MHz): δ (ppm): 1.39:s:6H; 2.15:s:3H; 4.40:d:2H; 6.82:up:3H; 7.11:mt:1H; 7.29:d:2H; 7.44-7.61:m:5H; 7.65:mt:1H; 8.72:t:1H.

Compound 60: $^1$H NMR: DMSO-d$_6$ (250 MHz): δ (ppm): 1.42-4.82:up:4H; 2.02-2.40:up:4H; 4.40:d:2H; 7.29:d:2H; 7.44-7.63:up:7H; 7.68:mt:1H; 7.76:d:2H; 8.72:t:1H.

Compound 74: $^1$H NMR: DMSO-d$_6$ (250 MHz): δ (ppm): 4.71:d:2H; 6.96-7.80:up:10H; 8.0:d:2H; 9.33:t:1H.

Compound 82: $^1$H NMR: DMSO-d$_6$ (250 MHz): δ (ppm): 4.73:d:2H; 7.33:d:2H; 7.46-7.67:up:5H; 7.73:mt:1H; 8.03:dd:4H; 9.52:t:1H.

Compound 99: $^1$H NMR:DMSO-d$_6$ (250 MHz): δ (ppm): 1.41:s:6H; 3.70:s:3H; 4.45:d:2H; 6.81-7.06:up:5H; 7.09-7.24:up:3H; 7.42-7.67:up:4H; 8.80:t:1H.

The compounds of formula (I) possess very good in vitro affinity (IC50≦1.10-7 M) for human or rodent cannabinoid CB1 receptors, under the experimental conditions described by M. Rinaldi-Carmona et al. (FEBS Letters, 1994, 350, 240-244).

The antagonist nature of the compounds of formula (I) was demonstrated by the results obtained in models of inhibition of adenylate cyclase as described in M. Bouaboula et al., J. Biol. Chem., 1995, 270, 13973-13980, M. Rinaldi-Carmona et al., J. Pharmacol. Exp. Ther., 1996, 278, 871-878, and M. Bouaboula et al., J. Biol. Chem., 1997, 272, 22330-22339.

The interaction in vivo of a compound of formula (I) with the CB1 receptors present in the brain is determined in mice by means of the ex vivo test for binding of [3H]-CP55940 after intravenous injection or oral administration, as described in Rinaldi-Carmona M. et al., FEBS Letters (1994), 350, 240-244, Rinaldi-Carmona M. et al., Life Sciences (1995), 56, 1941-1947, and Rinaldi-Carmona M. et al., J. Pharmacol. Exp. Ther. 2004, 310, 905-914.

The interaction in vivo of a compound of formula (I) with the CB1 receptors present peripherally is determined in mice by means of the test for reversion of the inhibitory effect of CP55940 on gastrointestinal transit after oral administration, as described in Rinaldi-Carmona M. et al., J. Pharmacol. Exp. Ther. 2004, 310, 905-914.

The toxicity of the compounds of formula (I) is compatible with their use as medicaments.

Thus, according to another of its aspects, a subject of the invention provides medicaments for human or veterinary medicine which comprise a compound of formula (I), or an addition salt thereof with a pharmaceutically acceptable acid, or alternatively a solvate or a hydrate of the compound of formula (I).

Thus, the compounds according to the invention can be used in the treatment or prevention of diseases involving cannabinoid CB$_1$ receptors, in humans or in animals (in particular in mammals, including, in a non-limiting manner, dogs, cats, horses, cattle, and sheep).

For example, and in a nonlimiting manner, the compounds of formula (I) are of use as psychotropic medicaments, in particular for the treatment of psychiatric disorders including anxiety, depression, mood disorders, insomnia, delirium disorders, obsessive disorders, psychoses in general, schizophrenia, attention deficit hyperactivity disorders (ADHD) in hyperkinetic children, and also for the treatment of disorders associated with the use of psychotropic substances, in particular in the case of a substance abuse and/or dependence on a substance, including alcohol dependence and nicotine dependence.

The compounds of formula (I) according to the invention can be used as medicaments for the treatment of migraine, stress, diseases of psychosomatic origin, panic attacks, epilepsy, motor disorders, in particular dyskinesia or Parkinson's disease, shaking, and dystonia.

The compounds of formula (I) according to the invention can also be used as medicaments in the treatment of memory disorders, cognitive disorders, in particular in the treatment of senile dementia and Alzheimer's disease, and also in the treatment of attention or watchfulness disorders. Furthermore, the compounds of formula (I) can be used as neuroprotective agents, in the treatment of ischemia, cranial trauma and the treatment of acute or chronic neurodegenerative diseases: including chorea, Huntington's chorea, and Tourette's syndrome.

The compounds of formula (I) according to the invention can be used as medicaments in the treatment of pain: neuropathic pain, acute peripheral pain, chronic pain of inflammatory origin or pain induced by an anticancer treatment.

The compounds of formula (I) according to the invention can be used as medicaments in human or veterinary medicine, in the treatment and prevention of appetite disorders, appetence disorders (for sugars, carbohydrates, drugs, alcohols or any appetizing substance) and/or eating disorders, in particular for the treatment of obesity or bulimia and also for the treatment of type II diabetes or non-insulin-dependent diabetes and for the treatment of dyslipidemia and metabolic syndrome. Thus, the compounds of formula (I) according to the invention are of use for the treatment and prevention of obesity and the risks associated with obesity, in particular cardiovascular risks.

Furthermore, the compounds of formula (I) according to the invention can be used as medicaments in the treatment and prevention of gastrointestinal disorders, diarrhea disorders, ulcers, vomiting, blood urinary disorders, liver diseases such as chronic cirrhosis, fibrosis, hepatic steatosis, steatohepatitis; and also disorders of endocrine origin, cardiovascular disorders, hypotension, atherosclerosis, hemorrhagic shock, septic shock, asthma, chronic bronchitis, chronic obstructive pulmonary diseases, Raynaud's syndrome, glaucoma, fertility disorders, interruption of pregnancy, preterm labor, inflammatory phenomena, immune system diseases, in particular autoimmune diseases and neuroinflammatory diseases such as rheumatoid arthritis, reactional arthritis, diseases resulting in demyelination, multiple sclerosis, infectious and viral diseases such as encephalitis, cerebral strokes, and also as medicaments for anticancer chemotherapy, for the treatment of Guillain-Barré syndrome, and for the treatment of bone diseases and osteoporosis.

According to the present invention, the compounds of formula (I) are of most particular use for the treatment of psychiatric disorders, especially schizophrenia, attention and watchfulness disorders, attention and hyperactivity disorders (ADHD) in hyperkinetic children; for the treatment of appetite and obesity disorders; for the treatment of memory deficits and cognitive disorders; for the treatment of dependence on and withdrawal from a substance, especially alcohol dependence, nicotine dependence, alcohol withdrawal, and tobacco withdrawal; and acute or chronic neurodegenerative diseases.

More particularly, the compounds of formula (I) according to the present invention are of use in the preparation of medicaments which are useful in the treatment and prevention of appetite disorders, appetence disorders, metabolic disorders, obesity, type II diabetes, metabolic syndrome, dislipidemia, gastro-intestinal disorders, inflammatory phenomena, immune system diseases, psychotic disorders, alcohol dependence and nicotine dependence.

According to one of its aspects, the present invention relates to the use of a compound of formula (I), or one of its addition salts with a pharmaceutically acceptable acid, or its solvates or hydrates, for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or one of its addition salts with a pharmaceutically acceptable acid, or a solvate or hydrate of said compound, and also at least one pharmaceutically acceptable excipient.

Said excipients are selected, according to the pharmaceutical form and the method of administration desired, from the usual excipients known to those skilled in the art.

The pharmaceutical compositions according to the present invention may contain, along with a compound of formula (I), one (or more) other active ingredient(s) of use in the treatment of the disorders and diseases indicated above.

Accordingly, the present invention also provides pharmaceutical compositions containing a compound of formula (I) according to the present invention combined with one (or more) active ingredient(s) selected from one of the following therapeutic classes:

another cannabinoid $CB_1$ receptor antagonist or allosteric cannabinoid $CB_1$ receptor modulators;
a cannabinoid $CB_2$ receptor modulator;
an angiotensin II $AT_1$ receptor antagonist;
a converting enzyme inhibitor;
a calcium antagonist;
a diuretic;
a beta-blocker;
an antihyperlipidemia agent or an antihyper-cholesterolemia agent;
an antidiabetic;
another anti-obesity agent or agent acting on metabolic disorders;
a nicotine agonist or a partial nicotine agonist;
an antidepressant, an antipsychotic or an anxiolytic;
an anticancer agent or an antiproliferative agent;
an opioid antagonist;

and also:

a memory-improving agent;
an agent for use in the treatment of alcoholism or withdrawal symptoms;
an agent of use for treating osteoporosis;
a nonsteroidal or steroidal anti-inflammatory;
an anti-infective;
an analgesic;
an antiasthmatic.

The expression "angiotensin II $AT_1$ receptor antagonist" is intended to mean a compound such as candesartan, cilexitil, eprosartan, irbesartan, losartan potassium, olmesartan medoxomil, telmisartan or valsartan, each of these compounds themselves possibly being combined with a diuretic such as hydrochlorothiazide.

The term "converting enzyme inhibitor" is intended to mean a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, each of these compounds itself possibly being combined with a diuretic such as hydrochlorothiazide or indapamide, or with a calcium antagonist such as amlodipine, diltiazem, felodipine or verapamil.

The term "calcium antagonist" is intended to mean a compound such as amlodipine, aranidipine, benidipine, bepridil, cilnidipine, diltiazem, efonidipine hydrochloric ethanol, fasudil, felodipine, isradipine, lacidipine, lercanidipine hydrochloride, manidipine, mibrefradil hydrochloride, nicardipine, nifedipine, nilvadipine, nimodipine, nisoldipine, nitrendipine, terodiline or verapamil.

The term "beta-blocker" is intended to mean a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertatolol, tilisolol, timolol, xamoterol or xibenolol.

The term "antihyperlipidemia agent" or "antihypercholesterolemia agent" is intended to mean a compound selected from fibrates such as alufibrate, beclobrate, bezafibrate, ciprofibrate, clinofibrate, clofibrate, etofibrate or fenofibrate; statins (HMG-COA reductase inhibitors), such as atorvastatin, fluvastatin sodium, lovastatin, pravastatin, rosuvastatin or simvastatin, or a compound such as acipimox, aluminum nicotinate, azacosterol, cholestyramine, dextrothyroxine, meglutol, niceritrol, nicoclonate, nicotinic acid, beta-sitosterol or tiadenol.

The term "antidiabetic" is intended to mean a compound belonging to one of the following classes: sulfonylureas, biguanidines, alpha-glucosidase inhibitors, thiazolidinediones, metiglinides, such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose, and also insulin and insulin analogs.

The term "another anti-obesity agent or agent acting on metabolic disorders" is intended to mean a compound such as amfepramone, benfluorex, benzphetamine, indanorex, mazindole, mefenorex, methamphetamine, D-norpseudoephedrine, sibutramine, a topiramate, a lipase inhibitor (orlistat or cetilistat), a PPAR agonist (peroxisome proliferator activated receptor agonist), a dopamine agonist, a leptin receptor agonist, a serotonin reuptake inhibitor, a beta-3 agonist, a CCK-A agonist, an NPY inhibitor, an MC4 receptor agonist, an MCH (Melanine Concentrating Hormone) receptor antagonist, an orexin agonist, a phosphodiesterase inhibitor, an 11βHSD (11-β-hydroxy steroid dehydrogenase) inhibitor, a DPP-IV (dipeptidyl peptidase IV) inhibitor, a histamine H3 agonist (or inverse agonist), a CNTF (Ciliary Neurotrophic Factor) derivative, a GHS (Growth Hormone Secretagogue) receptor agonist, a ghrelin modulator, a diacylglycerol acyltransferase (DGAT) inhibitor, a phosphodiesterase (PDE) inhibitor, a thyroid hormone antagonist, a glucocorticoid receptor antagonist, a stearoyl-Co-A-desaturase (SCD) inhibitor, a phosphate, glucose, fatty acid or dicarboxylate transport inhibitor, a $5HT_2$ antagonist, a $5HT_6$ antagonist or a bombesin agonist.

The term "opioid antagonist" is intended to mean a compound such as naltrexone, naloxone or nalmefene.

The expression "agent for use in the treatment of alcoholism and withdrawal symptoms" is intended to mean acamprosate, benzodiazepines, beta-blockers, clonidine or carbamazepine.

The expression "agent of use for treating osteoporosis" is intended to mean, for example, bisphosphonates such as etidronate, clodronate, tiludronate or risedronate.

According to the present invention, other compounds with antihyperlipidemia, antihypercholesterolemia, antidiabetic or anti-obesity properties may also be combined. More particularly, compounds belonging to one of the following classes may be combined:

PTP 1B (protein tyrosine phosphase-1B) inhibitors, VPAC 2 receptor agonists, GLK modulators, retinoid modulators, glycogen phosphorylase (HGLPa) inhibitors, glucagon antagonists, glucose-6-phosphate inhibitors, pyruvate dehydrogenase kinase (PKD) activators, RXR, FXR or LXR modulators, SGLT (sodium dependent glucose transporter) inhibitors, CETP (cholesteryl ester transfer protein) inhibitors, squalene synthetase inhibitors, squalene epoxidase inhibitors, triglyceride synthesis inhibitors, LDL (low density lipoprotein) receptor inducers, IBAT inhibitors, FBPase (fructose-1,6-biphosphatase) inhibitors, CART (cocaine-amphetamine-regulated transcript) modulators, MC4 (melanocortin 4) modulators, and orexin receptor antagonists.

According to another aspect of the invention, the compound of formula (I), or one of its addition salts with a pharmaceutically acceptable acid, or one of its solvates or hydrates, and the other active principle combined, may be administered simultaneously, separately or spread out over time.

"Simultaneous use" means the administration of the compounds of the composition according to the invention in the same, single pharmaceutical form.

"Separate use" means the administration at the same time of the two compounds of the composition according to the invention, each in a distinct pharmaceutical form.

"Use spread out over time" means the successive administration of the first compound of the composition of the invention, in one pharmaceutical form, then of the second compound of the composition according to the invention, in a distinct pharmaceutical form. In this case, the interval of time elapsed between the administration of the first compound of the composition according to the invention and the administration of the second compound of the same composition according to the invention does not generally exceed 24 hours.

In the pharmaceutical compositions of the present invention for oral, sublingual, subcutaneous, intra-muscular, intravenous, topical, local, intratracheal, intranasal, transdermal or rectal administration, the active ingredient of formula (I) above or one of its addition salts with a pharmaceutically acceptable acid, or the possible solvate or hydrate thereof, may be administered in a unit administration form, as a mixture with standard pharmaceutical excipients, to animals and to human beings for the prophylaxis or treatment of the above disorders or diseases.

The appropriate unit administration forms include forms for oral administration, such as tablets, soft or hard gel capsules, powders, granules and oral solutions or suspensions, sublingual, buccal, intratracheal, intra-ocular and intranasal administration forms, forms for administration by inhalation, topical, transdermal, subcutaneous, intramuscular or intravenous administration forms, rectal administration forms and implants. For topical application, the compounds according to the invention may be used in creams, gels, ointments or lotions.

By way of example, a unit administration form for a compound according to the invention in tablet form may comprise the following constituents:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

For oral administration, the dose of active principle administered per day may reach from 0.01 to 100 mg/kg, in one or more dosage intakes, preferably 0.02 to 50 mg/kg.

There may be specific cases where higher or lower dosages are appropriate; such dosages do not depart from the scope of the invention. According to the usual practice, the dosage appropriate to each patient is determined by the physician according to the method of administration and the weight and response of said patient.

According to another of its aspects, the present invention also relates to a method of treating the pathologies indicated above, which comprises the administration to a patient of an effective dose of a compound according to the invention, or one of its addition salts with a pharmaceutically acceptable acid, or its hydrates or solvates.

What is claimed is:

1. A compound of the formula (I):

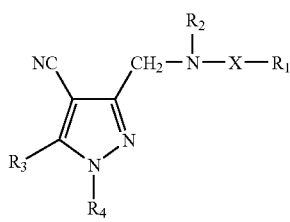

in which:

X represents

group, a

group, or a —SO$_2$—N(R$_5$)— group; R$_1$ represents:
a (C$_1$-C$_{12}$)alkyl substituted one or more times by substituents selected independently from:
  a) a fluorine atom;
  b) a (C$_1$-C$_4$)alkoxy;
  c) a (C$_3$-C$_7$)cycloalkyl;
  d) a phenyl which is unsubstituted or substituted one or more times by substituents selected independently from a halogen atom, a group Alk, and a group OAlk;
  e) a phenoxy, a phenylthio or a phenylsulfonyl in each of which the phenyl is unsubstituted or substituted one or more times by substituents selected independently from a halogen atom, a group Alk, and a group OAlk;
  f) a pyridyloxy in which the pyridyl is unsubstituted or substituted one or more times by substituents selected independently from a halogen atom, a group Alk and a group OAlk;
  g) a heterocyclic aromatic radical selected from a pyrrolyl, an imidazolyl, a pyrazolyl, a furyl, a thienyl, an oxazolyl, and a pyridyl, said radical being unsubstituted or substituted one or more times by substituents selected independently from a halogen atom, a group Alk, and a group OAlk;

a (C$_3$-C$_{12}$) nonaromatic carbocyclic radical or substituted one or more times by substituents selected independently from a halogen atom, a group Alk, a group OAlk, a phenyl or a phenylsulfonyl, in both of which the phenyl is itself unsubstituted or substituted by a halogen atom;

a phenyl which is or substituted one or more times by substituents selected independently from a group Alk, a group OAlk, a methylenedioxy, a group —NHAlk, a group —N(Alk)$_2$, a cyano, a nitro, a (C$_1$-C$_4$)alkylcarbonyl group, a (C$_1$-C$_4$)alkoxy-carbonyl group, a phenyl, phenoxy, pyrrolyl, imidazolyl, pyrazolyl, oxazolyl, thiazolyl, triazolyl, thiadiazolyl and pyridyl radical, said radical being unsubstituted or substituted one or more times by a (C$_1$-C$_4$)alkyl;

a tetrahydronaphthyl which is unsubstituted or substituted by a (C$_1$-C$_4$)alkyl;

a 2,3-dihydrobenzofuranyl which is unsubstituted or substituted by a (C$_1$-C$_4$)alkyl;

a 3,4-dihydro-2H-pyranyl which is unsubstituted or substituted by a (C$_1$-C$_4$)alkyl;

a heterocyclic aromatic radical selected from a pyrrolyl, an imidazolyl, a pyrazolyl, a furyl, a thienyl, an oxazolyl, a pyridyl and a 1,3-benzothiazolyl, said radical being unsubstituted or substituted one or more times by substituents selected independently from a halogen atom, a group Alk, and a group OAlk;

R$_2$ represents a hydrogen atom or a (C$_1$-C$_4$)alkyl;

R$_3$ represents a phenyl which is unsubstituted or substituted one or more times by substituents selected independently from a halogen atom, a group Alk and a group OAlk;

R$_4$ represents a phenyl which is unsubstituted or substituted one or more times by substituents selected independently from a halogen atom, a group Alk, and a group OAlk;

R$_5$ represents a hydrogen atom or a (C$_1$-C$_4$)alkyl; and

Alk represents a (C$_1$-C$_4$)alkyl which is unsubstituted or substituted one or more times by a fluorine atom;

or a salt thereof.

2. The compound of claim 1, wherein —X— represents a —CO— group.

3. The compound of claim 1, wherein —X— represents a —CSNH— group.

4. The compound of claim 1, wherein —X— represents a —SO$_2$N(R$_5$)— group.

5. The compound of formula (I) of claim 1, wherein:

X represents a

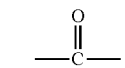

group or a

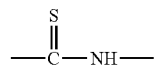

group;

R$_1$ represents:
a (C$_1$-C$_{12}$)alkyl which is mono- or disubstituted by substituents selected independently from:
  a) a fluorine atom
  b) a (C$_1$-C$_4$)alkoxy;
  c) a (C$_3$-C$_7$)cycloalkyl;

d) a phenyl which is unsubstituted or mono- or disubstituted by substituents selected independently from a halogen atom, a group Alk, and a group OAlk;
e) a phenoxy, a phenylthio or a phenylsulfonyl in each of which the phenyl is unsubstituted or mono- or disubstituted by substituents selected independently from a halogen atom, a group Alk, and a group OAlk;
f) a pyridyloxy in which the pyridyl is substituted by a group Alk;
g) a heterocyclic aromatic radical selected from a pyrrolyl;
a $(C_3-C_7)$cycloalkyl which is monosubstituted by a substituent selected from a group Alk, a group OAlk, and a phenyl or a phenylsulfonyl in both of which the phenyl is itself substituted by a halogen atom;
a bicyclo[2.2.1]heptyl;
a phenyl which is mono- or disubstituted by substituents selected independently from a group Alk, a group OAlk, a methylenedioxy, a group —N(Alk)$_2$, a cyano, a $(C_1-C_4)$alkylcarbonyl, a $(C_1-C_4)$alkoxycarbonyl, a phenyl and pyrrolyl radical;
a 2,3-dihydrobenzofuranyl;
a 3,4-dihydro-2H-pyranyl substituted by a $(C_1-C_4)$alkyl;
a heterocyclic aromatic radical selected from a pyrazolyl, a furyl, a thienyl and a 1,3-benzothiazolyl, said radical being unsubstituted or being monosubstituted or disubstituted with substituents selected independently from a halogen atom and a group Alk;
R$_2$ represents a hydrogen atom;
R$_3$ represents a phenyl which is monosubstituted by a halogen atom, or a group OAlk;
R$_4$ represents a phenyl which is mono- or disubstituted by a halogen atom;
R$_5$ represents a hydrogen atom or a $(C_1-C_4)$alkyl; and
Alk represents a $(C_1-C_4)$alkyl which is unsubstituted or substituted one or more times by a fluorine atom;
or a salt thereof.

6. The compound of formula (I) of claim 1, wherein:
X represents a

group or a

group;
R$_1$ represents:
a methoxy(phenyl)methyl, a cyclopentylmethyl, a cyclohexylmethyl, a cyclo-hexyl(phenyl)methyl, a (3,4-dimethoxyphenyl)methyl, a 2-(4-methylphenyl)ethyl, a 2-[4-(tri-fluoromethyl)phenyl]ethyl, a 2,2-diphenylethyl,
a 1-(4-chlorophenoxy)-1-methylethyl, a 1-(3-chlorophenoxy)-1-methylethyl, a 1-(4-chlorophenoxy)-1-methylethyl, a 1-(2-methylphenoxy)-1-methylethyl, a 1-(4-methylphenoxy)-1-methylethyl, a 1-methyl-1-[3trifluoromethyl)phenoxy]ethyl, a 1-(2-methoxyphenoxy)-1-methylethyl, a 1-(3-methoxyphenoxy)-1-methylethyl, a 1-[(4-chlorophenyl)thio]-1-methylethyl, a 1-[(4-chlorophenyl)sulfonyl]-1-methylethyl, a 1-methyl-1-[[5-(trifluoromethyl)pyridin-2-yl]oxy]ethyl, a 2,2-dimethyl-1-(1H-pyrrol-1-yl)propyl;
a 1-methylcyclopropyl, a 1-(4-chlorophenyl)cyclopentyl, a 1-[(4-chlorophenyl)sulfonyl]cyclopentyl, a 1-methylcyclohexyl, a 3-methoxycyclohexyl, a 4-methoxycyclohexyl, a 3,5-dimethylphenyl, a 4-tert-butylphenyl, a 4-(trifluoromethyl)-phenyl, a 3-methoxyphenyl, a 4-methoxyphenyl, a 4-(trifluoromethoxy)phenyl, a 3-phenoxyphenyl, a 4-phenoxyphenyl, a 1,3-benzodioxol-5-yl,
a 3-(dimethylamino)-phenyl, a 4-cyanophenyl, a 3-acetylphenyl, a 4-acetylphenyl, a 4-(methoxycarbonyl)phenyl, a 4-(1H-pyrrol-1-yl)phenyl; a 2,3-dihydro-1-benzofuran-5-yl, a 6-methyl-3,4-dihydro-2H-pyran-5-yl, a 3-tert-butyl-1-ethyl-1H-pyrazol-5-yl, a 2-furyl, 5-bromo-2-furyl, a 5-chloro-2-thienyl, a 5-methyl-2-thienyl or a 1,3-benzothiazol-6-yl:
R$_2$ represents a hydrogen atom;
R$_3$ represents a 4-chlorophenyl or a 4-methoxyphenyl; and
R$_4$ represents a 2-bromophenyl, a 2-chlorophenyl, a 2,4-dichlorophenyl;
or a salt thereof.

7. The compound of formula (I) of claim 1, which is selected from:
N-[[5-(4-chlorophenyl)-4-cyano-1-(2,4-dichlorophenyl)-1H-pyrazol-3-yl]methyl]-3,3-diphenylpropanamide;
N-[[5-(4-chlorophenyl)-4-cyano-1-(2,4-dichlorophenyl)-1H-pyrazol-3-yl]methyl]-4-(1H-pyrrol-1-yl)benzamide;
1-[[5-(4-chlorophenyl)-4-cyano-1-(2,4,dichlorophenyl)-1H-pyrazol-3-yl]methyl]-3-(3-methoxyphenyl)thiourea;
N-[[1-(2-chlorophenyl)-5-(4-chlorophenyl)-4-cyano-1H-pyrazol-3-yl]methyl]-3[4-(trifluoromethyl)phenyl]propanamide;
N-[[1-(2-chlorophenyl)-5-(4-chlorophenyl)-4-cyano-1H-pyrazol-3-yl]methyl]-3,3-diphenylpropanamide;
2-(2-chlorophenoxy)-N-[[1-(2-chlorophenyl)-5-(4-chlorophenyl)-4-cyano-1H-pyrazol-3-yl]methyl]-2-methylpropanamide;
N-[[1-(2-chlorophenyl)-5-(4-chlorophenyl)-4-cyano-1H-pyrazol-3-yl]methyl]-2-methyl-2-(2-methylphenoxy)propanamide;
N-[[1-(2-chlorophenyl)-5-(4-chlorophenyl)-4-cyano-1H-pyrazol-3-yl]methyl]-1-[(4-chlorophenyl)-sulfonyl]cyclopentanecarboxamide;
N-[[1-(2-chlorophenyl)-5-(4-chlorophenyl)-4-cyano-1H-pyrazol-3-yl]methyl]-4-(trifluoromethoxy)-benzamide;
N-[[1-(2-chlorophenyl)-5-(4-chlorophenyl)-4-cyano-1H-pyrazol-3-yl]methyl]-4-cyanobenzamide; and
2-(3-chlorophenoxy)-N-[[1-(2-chlorophenyl)-4-cyano-5-(4-methoxyphenyl)-1H-pyrazol-3-yl]methyl]-2-methylpropanamide;
or a salt thereof.

8. A process for preparing a compound of formula (I) of claim comprising: reacting a compound of formula (II):

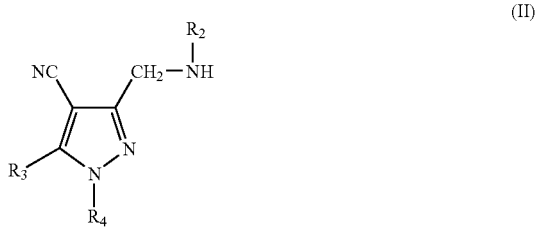

in which $R_2$, $R_3$, and $R_4$ are as defined in claim 1:
with an acid of formula (III):

$$HOOC-R_1 \qquad (III)$$

or a derivative thereof, wherein the derivative thereof is an acid chloride, an anhydride, a mixed anhydride, a $C_1$-$C_4$ alkylester in which the alkyl is straight or branched, or an activated ester of said acid of formula (III), and in which $R_1$ is as defined in claim 1, to prepare a compound of formula (I) in which —X— represents a —CO— group; or with an isothiocyanate of formula (VII):

$$S=C=N-R_1 \qquad (VII)$$

in which $R_1$ is defined in claim 1, to prepare a compound of formula (I) in which —X— represents a —CSNH— group; or with a sulfamoyl chloride a formula (XVII):

$$ClSO_2N(R_5)R_1 \qquad (XVII)$$

in which $R_1$ and $R_5$ are as defined in claim 1 to prepare a compound of formula (I), in which —X— represents a group —$SO_2N(R_5)$.

9. A pharmaceutical composition comprising a compound of formula (I) according to claim 1 or a pharmaceutically acceptable salt thereof in combination with at least one pharmaceutically acceptable excipient.

10. A pharmaceutical composition comprising a compound of formula (I) according to claim 2 or a pharmaceutically acceptable salt thereof in combination with at least one pharmaceutically acceptable excipient.

11. A pharmaceutical composition comprising a compound of formula (I) according to claim 3 or a pharmaceutically acceptable salt thereof in combination with at least one pharmaceutically acceptable excipient.

12. A pharmaceutical composition comprising a compound of formula (I) according to claim 4 or a pharmaceutically acceptable salt thereof in combination with at least one pharmaceutically acceptable excipient.

13. A pharmaceutical composition comprising a compound of formula (I) according to claim 5 or a pharmaceutically acceptable salt thereof in combination with at least one pharmaceutically acceptable excipient.

14. A pharmaceutical composition comprising a compound of formula (I) according to claim 6 or a pharmaceutically acceptable salt thereof in combination with at least one pharmaceutically acceptable excipient.

15. A pharmaceutical composition comprising a compound of formula (I) according to claim 7 or a pharmaceutically acceptable salt thereof in combination with at least one pharmaceutically acceptable excipient.

16. A method of treating pain, comprising administering to a patient in need of said treatment a therapeutically effective amount of a compound of formula (I) according to claim 1 or a pharmaceutically acceptable salt thereof.

* * * * *